United States Patent [19]

Iwasawa et al.

[11] Patent Number: 5,981,573
[45] Date of Patent: Nov. 9, 1999

[54] N,N-DISUBSTITUTED AMIC ACID DERIVATIVES

[75] Inventors: Yoshikazu Iwasawa; Tetsuya Aoyama; Kumiko Kawakami; Sachie Arai; Toshihiko Satoh; Yoshiaki Monden, all of Tsukuba, Japan

[73] Assignee: Banyu Pharmaceutical Co., Ltd., Tokyo, Japan

[21] Appl. No.: 09/117,532

[22] PCT Filed: Feb. 7, 1997

[86] PCT No.: PCT/JP97/00305

§ 371 Date: Aug. 4, 1998

§ 102(e) Date: Aug. 4, 1998

[87] PCT Pub. No.: WO97/29074

PCT Pub. Date: Aug. 14, 1997

[30] Foreign Application Priority Data

Feb. 7, 1996 [JP] Japan ................................. 8-045503

[51] Int. Cl.⁶ ..................... C07D 307/54; A61K 31/34
[52] U.S. Cl. ..................... 514/466; 514/338; 514/471; 546/283.7; 549/60; 549/435; 549/487; 560/20; 560/39; 560/41; 562/444; 562/450
[58] Field of Search ........................ 549/487; 560/39, 560/41; 562/444, 450; 514/466

[56] References Cited

U.S. PATENT DOCUMENTS

| | | | |
|---|---|---|---|
| 5,488,149 | 1/1996 | Nomoto et al. ........................ | 562/449 |
| 5,606,101 | 2/1997 | Nomoto et al. ........................ | 560/193 |
| 5,616,803 | 4/1997 | Nomoto et al. ........................ | 564/337 |
| 5,643,958 | 7/1997 | Iwasawa et al. ....................... | 514/568 |
| 5,777,150 | 7/1998 | Nomoto et al. ........................ | 560/60 |
| 5,849,747 | 12/1998 | Iwasawa et al. ....................... | 549/487 |

FOREIGN PATENT DOCUMENTS

| | | |
|---|---|---|
| 7-138214 | 5/1995 | Japan . |
| WO 96/05168 | 2/1996 | WIPO . |
| WO 96/05169 | 2/1996 | WIPO . |

*Primary Examiner*—Bernard Dentz
*Attorney, Agent, or Firm*—Oblon, Spivak, McClelland, Maier & Neustadt, P.C.

[57] ABSTRACT

A compound represented by general formula (I) or a pharmaceutically acceptable salt or ester thereof:

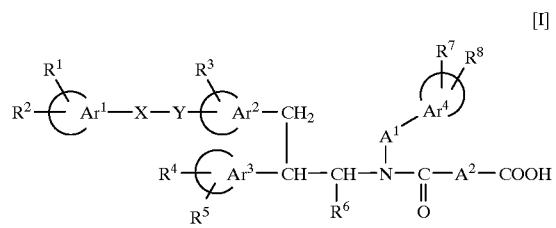

[wherein each of $Ar^1$, $Ar^2$, $Ar^3$ and $Ar^4$ is an aryl group or an aromatic heterocyclic group; $A^1$ is a $C_{2-6}$ chain hydrocarbon group or a group represented by $—A^{1a}—W^1—A^{1b}—$ (wherein $W^1$ is an oxygen atom, a sulfur atom, an ethynylene group, a cyclopropylene group or a group represented by $—NR^W—$; $A^2$ is a $C_{2-8}$ chain hydrocarbon group; each of X and Y is an oxygen atom, a sulfur atom, a carbonyl group or a group represented by $—CHR^a—$ or by $—NR^b—$, or X and Y together represent a vinylene group or an ethynylene group; each of $R^1$, $R^2$, $R^3$, $R^7$ and $R^8$ is a hydrogen atom, a halogen atom, a hydroxyl group, a lower alkyl group, a lower alkenyl group or a lower alkoxy group; each of $R^4$ and $R^5$ is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; and $R^6$ is a lower alkyl group, provided that when one of X and Y is an oxygen atom, a sulfur atom or a group represented by $—NR^b—$, the other is a carbonyl group or a group represented by $—CHR^a—$ and an antitumor agent comprising it as an active ingredient.

9 Claims, No Drawings

N,N-DISUBSTITUTED AMIC ACID DERIVATIVES

TECHNICAL FIELD

The present invention relates novel N,N-disubstituted amic acid derivatives. More particularly, the N,N-disubstituted amic acid derivatives of the present invention inhibit protein-farnesyl transferase (PFT) in vivo thereby to suppress function of oncogene protein Ras and thus present antitumor activities, etc., and they are thus useful in the pharmaceutical field.

BACKGROUND ART

The ras oncogene is activated by mutation, and its translation product Ras protein plays an important role in transformation of normal cells to cancer cells. Such activation of ras oncogene is observed in many cancers such as colorectal cancers or pancreatic cancers, and the proportion thereof is reported to reach about 20% of the total human cancers. Accordingly, it is expected that canceration can be suppressed and antitumor effects can be obtained by suppressing such activation of ras oncogene or by inhibiting the function of Ras protein as its product.

Recently, it has been found that farnesyl-modification of Ras protein itself is essential for function of Ras protein, and it is possible to suppress localization of Ras protein at the plasma membrane by inhibiting this farnesyl-modification and thereby to inhibit transformation to cancer cells. The protein-farnesyl transferase (PFT) is an enzyme which catalyses this farnesyl-modification of Ras protein, and by inhibiting this enzyme, it is possible to suppress function of carcinogenic Ras protein. Further, this enzyme contributes to farnesyl-modification of only very limited proteins in vivo. Accordingly, the inhibitor for such an enzyme is expected to be a safe and highly selective antitumor agent. From such a viewpoint, many PFT inhibitors have been developed in recent years (Cell, vol. 57, pp. 1167–1177 (1989); Proc. Natl. Acad. Sci., vol. 86, pp. 8323–8327 (1989); ditto, vol. 90, pp. 2281–2285 (1993); Science, vol. 245, pp. 379–385 (1989); ditto, vol. 260, pp. 1934–1937 (1993); ditto, vol. 260, pp. 1937–1942 (1993); J. Biol. Chem., vol. 266, pp. 15575–15578 (1991); J. Antibiotics, vol. 46, pp. 222–227 (1993); Natur Medicine, vol. 1, pp. 792–797 (1995); JP-A-5-201869; JP-A-5-213992).

Further, it has recently been found by a research by the present inventors that these PFT inhibitors can block the reactivation of static viruses by suppressing development of matured Ras proteins and are useful as anti-AIDS (HIV) agents (PCT/JP95/02489).

However, up to now, all of the reported PFT inhibitors have had some problems for development as medicines, such that the activities are low in cells, and the effects in vivo are inadequate.

DISCLOSURE OF THE INVENTION

It is an object of the present invention to provide a novel antitumor agent or an anti-AIDS agent which inhibits the protein-farnesyl transferase (PFT) thereby to inhibit functional manifestation of oncogene protein Ras and which thus provides antitumor or anti-AIDS effects.

The present inventors have found that a compound represented by general formula (I) or a pharmaceutically acceptable salt or ester thereof:

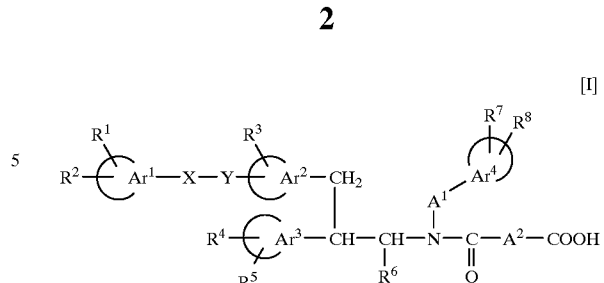

[wherein each of

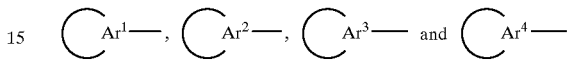

which are the same or different, is an aryl group or an aromatic heterocyclic group; $A^1$ is a $C_{2-6}$ chain hydrocarbon group which may have substituent(s) selected from the group consisting of a halogen atom, a lower alkyl group, an oxo group, a lower hydroxyalkyl group and a lower alkoxy group or a group represented by $-A^{1a}-W^1-A^{1b}-$ (wherein $A^{1a}$ is a $C_{1-5}$ chain hydrocarbon group which may have substituent(s) selected from the group consisting of a halogen atom, a lower alkyl group, an oxo group, a lower hydroxyalkyl group and a lower alkoxy group; $A^{1b}$ is a single bond or a $C_{1-4}$ chain hydrocarbon group which may have substituent(s) selected from the group consisting of a halogen atom, a lower alkyl group, an oxo group, a lower hydroxyalkyl group and a lower alkoxy group; $W^1$ is an oxygen atom, a sulfur atom, an ethynylene group, a cyclopropylene group or a group represented by $-NR^W-$; and $R^W$ is a hydrogen atom or a lower alkyl group); $A^2$ is a $C_{2-8}$ chain hydrocarbon group which may have substituent(s) selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and an aralkyl group; each of X and Y which are the same or different, is an oxygen atom, a sulfur atom, a carbonyl group or a group represented by $-CHR^a-$ (wherein $R^a$ is a hydrogen atom or a lower alkyl group) or by $-NR^b-$ (wherein $R^b$ is a hydrogen atom or a lower alkyl group), or X and Y together represent a vinylene group or an ethynylene group; each of $R^1$, $R^2$, $R^3$, $R^4$ and $R^8$ which are the same or different, is a hydrogen atom, a halogen atom, a hydroxyl group, a lower alkyl group, a lower alkenyl group or a lower alkoxy group; each of $R^4$ and $R^5$ which are the same or different, is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; and $R^6$ is a lower alkyl group, provided that when one of X and Y is an oxygen atom, a sulfur atom or a group represented by $-NR^b-$ (wherein $R^b$ is the same as defined above), the other is a carbonyl group or a group represented by $-CHR^a-$ (wherein $R^a$ is the same as defined above)], inhibits the protein-farnesyl transferase (PFT) thereby to suppress function of oncogene protein Ras, and thus is useful as an antitumor agent or an anti-AIDS agent. The present invention has been accomplished on the basis of this discovery.

Thus, the present invention relates to a compound represented by general formula (I), or its pharmaceutically acceptable salt or ester, as well as its application.

Symbols and terms used in this specification will be explained.

The aryl group means a phenyl group, a naphthyl group or an anthryl group. A phenyl group or a naphthyl group is preferred.

The aromatic heterocyclic group means a 5-membered or 6-membered monocyclic aromatic heterocyclic group containing one or two hetero atoms, which are the same or different, selected from the group consisting of an oxygen atom, a nitrogen atom and a sulfur atom, or a fused aromatic heterocyclic group having such a monocyclic aromatic heterocyclic group fused with the above-mentioned aryl group or having the same or different such monocyclic aromatic heterocyclic groups fused with each other, which may, for example, be a pyrrolyl group, an imidazolyl group, a pyrazolyl group, a pyridyl group, a pyrazinyl group, a pyrimidinyl group, a pyridazinyl group, an oxazolyl group, an isoxazolyl group, a furyl group, a thienyl group, a thiazolyl group, an isothiazolyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthylidinyl group, a quinoxalinyl group, a quinazolinyl group, a cinnolinyl group or a pteridinyl group. Among them, a furyl group, a thienyl group, a pyridyl group, a pyrimidinyl group, an oxazolyl group, an isoxazolyl group, a thiazolyl group, a benzofuranyl group, a benzothienyl group, a benzimidazolyl group, a benzoxazolyl group, a benzothiazolyl group or a quinolyl group is preferred.

The lower alkyl group means a $C_{1-6}$ linear or branched alkyl group, which may, for example, be a methyl group, an ethyl group, a propyl group, an isopropyl group, a butyl group, a sec-butyl group, a tert-butyl group, a pentyl group or a hexyl group. Among them, a methyl group or an ethyl group is preferred.

The lower alkenyl group means a $C_{2-6}$ linear or branched alkenyl group, such as a vinyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group or a 4-pentenyl group.

The lower hydroxyalkyl group means the above-mentioned lower alkyl group having a hydroxyl group, i.e. a $C_{1-6}$ hydroxyalkyl group, such as a hydroxymethyl group, a hydroxyethyl group, a hydroxypropyl group or a hydroxybutyl group. Among them, a hydroxymethyl group or a hydroxyethyl group is preferred.

The lower alkoxy group means a $C_{1-6}$ alkoxy or alkylenedioxy group, which may, for example, be a methoxy group, an ethoxy group, a propoxy group, an isopropoxy group, a butoxy group, a tert-butoxy group, a methylenedioxy group, an ethylenedioxy group or a trimethylenedioxy group. Among them, a methoxy group, an ethoxy group or a methylenedioxy group is preferred.

The lower carboxyalkyl group means the above-mentioned lower alkyl group having a carboxyl group, i.e. a $C_{1-7}$ carboxyalkyl group, such as a carboxymethyl group, a carboxyethyl group, a carboxypropyl group or a carboxybutyl group. Among them, a carboxymethyl group or a carboxyethyl group is preferred.

The aralkyl group means the above-mentioned lower alkyl group having the above-mentioned aryl group, such as a benzyl group, a phenethyl group, a 3-phenylpropyl group, a 1-naphthylmethyl group, a 2-naphthylmethyl group or a 1-(2-naphthyl)ethyl group. Among them, a benzyl group, a phenethyl group or a 2-naphthylmethyl group is preferred.

The chain hydrocarbon group means a linear saturated aliphatic hydrocarbon group, or a linear unsaturated aliphatic hydrocarbon group having one or more, preferably one or two double bonds, at optional positions on the carbon chain.

The saturated aliphatic hydrocarbon group may, for example, be a methylene group, an ethylene group, a trimethylene group, a tetramethylene group, a pentamethylene group, a hexamethylene group, a heptamethylene group or an octamethylene group.

The unsaturated aliphatic hydrocarbon group may, for example, be a vinylene group, a propenylene group, a 1-butenylene group, a 2-butenylene group, a 1,3-butadienylene group, a 1-pentenylene group, a 2-pentenylene group, a 1,3-pentadienylene group, a 1,4-pentadienylene group, a 1-hexenylene group, a 2-hexenylene group, a 3-hexenylene group, a 1,3-hexadienylene group, a 1,4-hexadienylene group, a 1,5-hexadienylene group, a 1,3,5-hexatrienylene group, a 1-heptenylene group, a 2-heptenylene group, a 3-heptenylene group, a 1,3-heptadienylene group, a 1,4-heptadienylene group, a 1,5-heptadienylene group, a 1,6-heptadienylene group, a 1,3,5-heptatrienylene group, a 1-octenylene group, a 2-octenylene group, a 3-octenylene group, a 4-octenylene group, a 1,3-octadienylene group, a 1,4-octadienylene group, a 1,5-octadienylene group, a 1,6-octadienylene group, a 1,7-octadienylene group, a 2,4-octadienylene group, a 2,5-octadienylene group, a 2,6-octadienylene group, a 3,5-octadienylene group, a 1,3,5-octatrienylene group, a 2,4,6-octatrienylene group or a 1,3,5,7-octatetraenylene group.

The halogen atom may be a fluorine atom, a chlorine atom, a bromine atom or an iodine atom. For example, a fluorine atom or a chlorine atom is preferred.

The lower alkoxycarbonyl group means a $C_{1-7}$ alkoxycarbonyl group, such as a methoxycarbonyl group, an ethoxycarbonyl group, a propoxycarbonyl group, a butoxycarbonyl group, a pentoxycarbonyl group, an isopropoxycarbonyl group, an isobutoxycarbonyl group, a tert-butoxycarbonyl group, an isopentoxycarbonyl group, a neopentoxycarbonyl group, cyclopropoxycarbonyl group, a cyclobutoxycarbonyl group, a cyclopentoxycarbonyl group, a cyclohexyloxycarbonyl group, a 1-methylcyclopropoxycarbonyl group, a 1-methylcyclopentoxycarbonyl group, a 1-methylcyclobutoxycarbonyl group, a 2-methylcyclobutoxycarbonyl group, a 1,1-dimethylpropoxycarbonyl group, a 1,2-dimethylpropoxycarbonyl group, a 1-ethylpropoxycarbonyl group, a 1,2-dimethylcyclopropoxycarbonyl group, a 2,2-dimethylcyclopropoxycarbonyl group, a 2,3-dimethylcyclopropoxycarbonyl group, a 1,2-dimethylcyclobutoxycarbonyl group, a 1,3-dimethylcyclobutoxycarbonyl group, a 2,2-dimethylcyclobutoxycarbonyl group, a 2,3-dimethylcyclobutoxycarbonyl group, a 3,3-dimethylcyclobutoxycarbonyl group, a 2,4-dimethylcyclobutoxycarbonyl group, a 2,3-dimethylcyclopentoxycarbonyl group, a 2,4-dimethylcyclopentoxycarbonyl group or a 2,5-dimethylcyclopentoxycarbonyl group. Among them, a methoxycarbonyl group, an ethoxycarbonyl group, a propoxycarbonyl group, an isopropoxycarbonyl group, a tert-butoxycarbonyl group, a cyclopropoxycarbonyl group, a cyclobutoxycarbonyl group, a cyclopentoxycarbonyl group, a 1-methylcyclopropoxycarbonyl group, a 1-methylcyclopentoxycarbonyl group, a 1-methylcyclobutoxycarbonyl group, a 1,1-dimethylpropoxycarbonyl group or a 1,2-dimethylpropoxycarbonyl group is preferred.

The lower alkenyloxycarbonyl group means a $C_{3-7}$ alkenyloxycarbonyl group such as an allyloxycarbonyl group, a 2-butenyloxycarbonyl group, a 1-methyl-2-propenyloxycarbonyl group, a 3-methyl-2-butenyloxycarbonyl group, a 1-cyclobutenyloxycarbonyl group, a 2-cyclobutenyloxycarbonyl group, a 1-cyclopentenyloxycarbonyl group or a 2-cyclopentenyloxycarbonyl group. Among them, an allyloxycarbonyl group or a 1-methyl-2-propenyloxycarbonyl group is preferred.

The lower alkylcarbamoyl group means a carbamoyl group mono-substituted or di-substituted by the above-mentioned lower alkyl group, such as a methylcarbamoyl group, an ethylcarbamoyl group, a dimethylcarbamoyl group or a diethylcarbamoyl group.

The lower fluoroalkyl group means the above-mentioned lower alkyl group having fluorine atom(s), i.e. a $C_{1-6}$ fluoroalkyl group, such as a fluoromethyl group, a difluoromethyl group, a trifluoromethyl group, a 1-fluoroethyl group, a 2-fluoroethyl group, a 2,2,2-trifluoroethyl group or a pentafluoroethyl group.

The salt of the compound represented by general formula (I) may be a pharmaceutically acceptable common salt, which may, for example, be a base-addition salt of the terminal carboxyl group or of a carboxyl group when $R^4$ and/or $R^5$ is a carboxyl group, or when a carboxyl group or a lower carboxyalkyl group is present on a chain hydrocarbon group represented by $A^2$ in formula (I), or an acid-addition salt of an amino group when $R^4$ and/or $R^5$ is an amino group, or of a basic aromatic heterocyclic ring when such a basic aromatic heterocyclic ring is present.

The base-addition salt may, for example, be an alkali metal salt such as a sodium salt or a potassium salt; an alkaline earth metal salt such as a calcium salt or a magnesium salt; an ammonium salt; or an organic amine salt such as a trimethylamine salt, a triethylamine salt, a dicyclohexylamine salt, an ethanolamine salt, a diethanolamine salt, a triethanolamine salt, a procaine salt or an N,N'-dibenzylethylenediamine salt.

The acid-addition salt may, for example, be an inorganic acid salt such as a hydrochloride, a sulfate, a nitrate, a phosphate or a perchlorate; an organic acid salt such as a maleate, a fumarate, a tartrate, a citrate, an ascorbate or a trifluoroacetate; or a sulfonic acid salt such as a methanesulfonate, an isethionate, a benzenesulfonate or a p-toluenesulfonate.

The ester of the compound represented by general formula (I) means a pharmaceutically acceptable common ester of the terminal carboxyl group or of a carboxyl group when $R^4$ and/or $R^5$ is a carboxyl group, or when a carboxyl group or a lower carboxyalkyl group is present on the chain hydrocarbon group represented by $A^2$ in formula (I). It may, for example, be an ester with a lower alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group or a cyclopentyl group, an ester with an aralkyl group such as a benzyl group or a phenethyl group, an ester with a lower alkenyl group such as an allyl group or a 2-butenyl group, an ester with a lower alkoxyalkyl group such as a methoxymethyl group, a 2-methoxyethyl group or a 2-ethoxyethyl group, an ester with a lower alkanoyloxyalkyl group such as an acetoxymethyl group, a pivaloyloxymethyl group or a 1-pivaloyloxyethyl group, an ester with a lower alkoxycarbonylalkyl group such as a methoxycarbonylmethyl group or an isopropoxycarbonylmethyl group, an ester with a lower carboxyalkyl group such as a carboxymethyl group, an ester with a lower alkoxycarbonyloxyalkyl group such as a 1-(ethoxycarbonyloxy)ethyl group or a 1-(cyclohexyloxycarbonyloxy)ethyl group, an ester with a lower carbamoyloxyalkyl group such as a carbamoyloxymethyl group, an ester with a phthalidyl group, or an ester with a (5-substituted-2-oxo-1,3-dioxol-4-yl)methyl group such as a (5-methyl-2-oxo-1,3-dioxol-4-yl)methyl group.

Further, when a hydroxyl group is present at the γ- or δ-position of the terminal carboxyl group or of a carboxyl group when such a carboxyl group or a lower carboxyalkyl group is present on the chain hydrocarbon group represented by $A^2$ in formula (I), such a hydroxyl group and a carboxyl group may form an intramolecular ester i.e. a 5-membered or 6-membered lactone ring Further, the compound of the present invention may have stereoisomers such as optical isomers, diastereomers or geometrical isomers, depending upon the form of its substituents. The compound of the present invention includes all of such stereoisomers and their mixtures. Among them, a compound represented by general formula (I-1):

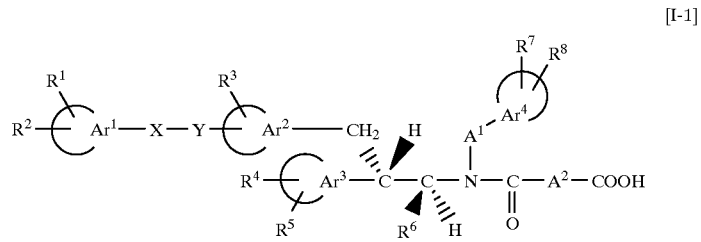

[wherein $\bigcirc_{Ar^1}-$, $\bigcirc_{Ar^2}-$, $\bigcirc_{Ar^3}-$, $\bigcirc_{Ar^4}-$, or general formula (I-2):

[I-2]

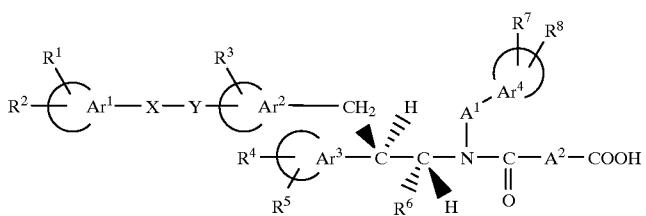

$A^1, A^2, X, Y, R^1, R^2, R^3, R^4, R^5, R^6, R^7$ and $R^8$ are the same as defined above] is preferred.

Among compounds represented by general formula (I), a compound wherein

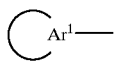

is a phenyl group or a thienyl group, a compound wherein

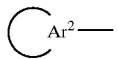

is a phenyl group, a thienyl group, a furyl group, a pyridyl group, a pyrimidinyl group, a thiazolyl group, an oxazolyl group, an isoxazolyl group, an isothiazolyl group or an oxadiazolyl group, a compound wherein

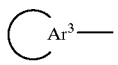

is a phenyl group, a thienyl group, a furyl group, a pyridyl group, a pyrimidinyl group, a thiazolyl group, an oxazolyl group, an isoxazolyl group, an isothiazolyl group or an oxadiazolyl group, and a compound wherein

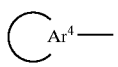

is a phenyl group, a thienyl group or a naphthyl group are preferred.

Each of X and Y which are the same or different, is an oxygen atom, a sulfur atom, a carbonyl group or a group represented by —CHR$^a$— (wherein R$^a$ is a hydrogen atom or a lower alkyl group) or by —NR$^b$— (wherein R$^b$ is a hydrogen atom or a lower alkyl group), or X and Y together represent a vinylene group or an ethynylene group. However, when one of X and Y is an oxygen atom, a sulfur atom or a group represented by —NR$^b$— (wherein R$^b$ is the same as defined above), the other is a carbonyl group or a group represented by —CHR$^a$— (wherein R$^a$ is the same as defined above).

Referring to general formula (I), a compound wherein X is a group represented by —NR$^b$— (wherein R$^b$ is the same as defined above), and Y is a carbonyl group, a compound wherein X is an oxygen atom, and Y is a group represented by —CHR$^a$— (wherein R$^a$ is the same as defined above), a compound wherein each of X and Y is a group represented by —CHR$^a$— (wherein R$^a$ is the same as defined above), or a compound wherein X and Y together represent a vinylene group, is preferred.

$A^1$ is a $C_{2-6}$ chain hydrocarbon group which may have substituent(s) selected from the group consisting of a halogen atom, a lower alkyl group, an oxo group, a lower hydroxyalkyl group and a lower alkoxy group or a group represented by —$A^{1a}$—$W^1$—$A^{1b}$— (wherein $A^{1a}$ is a $C_{1-5}$ chain hydrocarbon group which may have substituent(s) selected from the group consisting of a halogen atom, a lower alkyl group, an oxo group, a lower hydroxyalkyl group and a lower alkoxy group; $A^{1b}$ is a single bond or a $C_{1-4}$ chain hydrocarbon group which may have substituent(s) selected from the group consisting of a halogen atom, a lower alkyl group, an oxo group, a lower hydroxyalkyl group and a lower alkoxy group; $W^1$ is an oxygen atom, a sulfur atom, an ethynylene group, a cyclopropylene group or a group represented by —$NR^W$—; and $R^W$ is a hydrogen atom or a lower alkyl group).

The $C_{2-6}$ chain hydrocarbon group which may have substituent(s) selected from the group consisting of a halogen atom, a lower alkyl group, an oxo group, a lower hydroxyalkyl group and a lower alkoxy group, means the above-mentioned chain hydrocarbon group having from 2 to 6 carbon atoms, which is unsubstituted, or the above-mentioned chain hydrocarbon group having from 2 to 6 carbon atoms, which has substituent(s) at optional position (s) for substitution, and said substituent(s) may be one or more, preferably from one to three, which are the same or different and which are selected from the group consisting of a halogen atom, a lower alkyl group, an oxo group, a lower hydroxyalkyl group and a lower alkoxy group.

$A^{1a}$ means a $C_{1-5}$ chain hydrocarbon group which may have substituent(s) selected from the group consisting of a halogen atom, a lower alkyl group, an oxo group, a lower hydroxyalkyl group and a lower alkoxy group.

The $C_{1-5}$ chain hydrocarbon group which may have substituent(s) selected from the group consisting of a halogen atom, a lower alkyl group, an oxo group, a lower hydroxyalkyl group and a lower alkoxy group, means the above-mentioned chain hydrocarbon group having from 1 to 5 carbon atoms, which is unsubstituted, or the above-mentioned chain hydrocarbon group having from 1 to 5 carbon atoms, which has substituent(s) at optional position (s) for substitution, and the substituent(s) may be one or more, preferably from one to three, which are the same or different and which are selected from the group consisting of a halogen atom, a lower alkyl group, an oxo group, a lower hydroxyalkyl group and a lower alkoxy group.

$A^{1b}$ is a single bond or a $C_{1-4}$ chain hydrocarbon group which may have substituent(s) selected from the group consisting of a halogen atom, a lower alkyl group, an oxo group, a lower hydroxyalkyl group and a lower alkoxy group.

The $C_{1-4}$ chain hydrocarbon group which may have substituent(s) selected from the group consisting of a halogen atom, a lower alkyl group, an oxo group, a lower hydroxyalkyl group and a lower alkoxy group, means the above-mentioned chain hydrocarbon group having from 1 to 4 carbon atoms, which is unsubstituted, or the above-mentioned chain hydrocarbon group having from 1 to 4 carbon atoms, which has substituent(s) at optional position (s) for substitution, and the substituent(s) may be one or more, preferably from 1 to 3, which are the same or different and which are selected from the group consisting of a halogen atom, a lower alkyl group, an oxo group, a lower hydroxyalkyl group and a lower alkoxy group.

$W^1$ is an oxygen atom, a sulfur atom, an ethynylene group, a cyclopropylene group or a group represented by —$NR^W$—, and preferably an oxygen atom, an ethynylene group or a group represented by —$NR^W$—.

$R^W$ is a hydrogen atom or a lower alkyl group, and preferably a hydrogen atom.

As $A^1$, for example, a group represented by —$CH_2CH=CH$—, —$CH_2C\equiv C$—, —$CH_2CH_2O$— or —$CH_2CH_2CH_2$— is preferred.

$A^2$ means a $C_{2-8}$ chain hydrocarbon group which may have substituent(s) selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and an aralkyl group.

The $C_{2-8}$ chain hydrocarbon group which may have substituent(s) selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and an aralkyl group, means the above-mentioned chain hydrocarbon group having from 2 to 8 carbon atoms, which is unsubstituted, or the above-mentioned chain hydrocarbon group having from 2 to 8 carbon atoms, which has substituent(s) at optional position(s) for substitution, and the substituent(s) may be one or more, preferably from 1 to 3, which are the same or different and which are selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and an aralkyl group.

Compounds wherein $A^2$ is a group represented by formula (a):

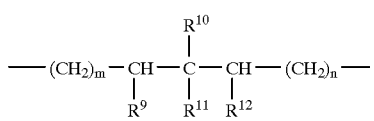

(wherein $R^9$ is a hydrogen atom, a hydroxyl group, a lower hydroxyalkyl group, a lower alkoxy group or a carboxyl group; $R^{10}$ is a hydrogen atom, a halogen atom, a hydroxyl group, a lower alkoxy group, a carboxyl group or a lower carboxyalkyl group; $R^{11}$ is a hydrogen atom, a lower hydroxyalkyl group, a carboxyl group, a lower alkoxycarbonyl group or a lower alkenyloxycarbonyl group; $R^{12}$ is a hydrogen atom, a halogen atom, a hydroxyl group or a carboxyl group; and each of m and n which may be the same or different is an integer of from 0 to 2) and compounds wherein $A^2$ is a group represented by formula (b):

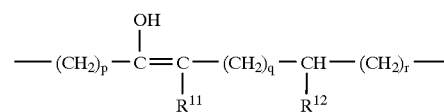

(wherein $R^{11}$ is a hydrogen atom, a lower hydroxyalkyl group, a carboxyl group, a lower alkoxycarbonyl group or a lower alkenyloxycarbonyl group; $R^{12}$ is a hydrogen atom, a hydroxyl group or a carboxyl group; p is 0 or 1; and each of q and r which are the same or different is an integer of from 0 to 2) are preferred.

When $A^2$ is represented by formula (a), $R^9$ is preferably a hydrogen atom, a hydroxyl group or a carboxyl group, $R^{10}$ is preferably a carboxyl group or a lower carboxyalkyl group such as a carboxymethyl group, $R^{11}$ and $R^{12}$ are preferably hydrogen atoms or carboxyl groups, and each of m and n which are the same or different is preferably 0 or 1.

When $A^2$ is represented by formula (b), $R^{11}$ is preferably a lower hydroxyalkyl group such as a hydroxymethyl group, a carboxyl group, a lower alkoxycarbonyl group such as a tert-butoxycarbonyl group or a lower alkenyloxycarbonyl group such as an allyloxycarbonyl group, $R^{12}$ is preferably a hydrogen atom, and p, q and r are preferably 0.

Further, it is well known that in the case of a compound having a partial structure represented by formula (b), there exist enol form and keto form tautomers, as shown below. The compound of the present invention includes such enol form and keto form isomers and their mixtures.

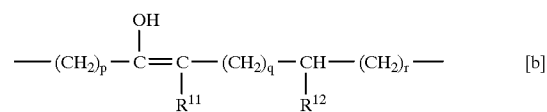

(Enol form)

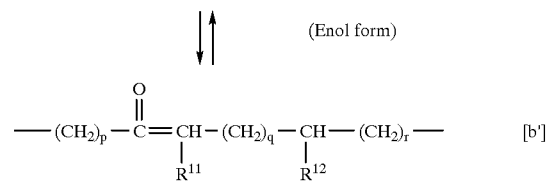

(Keto form)

(wherein $R^{11}$, $R^{12}$, p, q and r are the same as defined above)

Each of $R^1$ and $R^2$ which are the same or different, is a hydrogen atom, a halogen atom, a hydroxyl group, a lower alkyl group, a lower alkenyl group or a lower alkoxy group, and may be substituted at an optional position for substitution on the aryl group or the aromatic heterocyclic group represented by

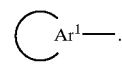

$R^3$ is a hydrogen atom, a halogen atom, a hydroxyl group, a lower alkyl group, a lower alkenyl group or a lower alkoxy group, and may be substituted at an optional position for substitution on the aryl group or the aromatic heterocyclic group represented by

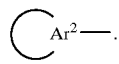

Further, in general formula (I), the group represented by

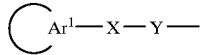

may also be substituted at an optional position for substitution on the above-mentioned aryl or aromatic heterocyclic group in the same manner as $R^3$.

Each of $R^4$ and $R^5$ which are the same or different, is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group. Each of them may be substituted at an optional position for substitution on the aryl or aromatic heterocyclic group represented by

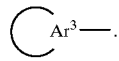

$R^6$ is preferably a methyl group, an ethyl group or a propyl group. Particularly preferred is a methyl group or an ethyl group.

Each of $R^7$ and $R^8$ which are the same or different, is a hydrogen atom, a halogen atom, a hydroxyl group, a lower alkyl group, a lower alkenyl group or a lower alkoxy group, and each of them may be substituted at an optional position for substitution on the aryl or aromatic heterocyclic group represented by

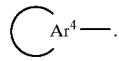

Now, processes for producing the compound of the present invention will be described.

The compound represented by general formula (I) of the present invention can be prepared, for example, by the following process 1, 2, 3, 4, 5 or 6.

Process 1

The compound represented by general formula (I) can be prepared by reacting a compound represented by general formula (II):

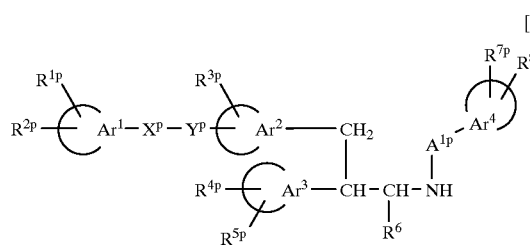

[wherein each of

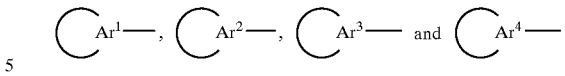

which are the same or different, is an aryl group or an aromatic heterocyclic group; $A^{1p}$ is a $C_{2-6}$ chain hydrocarbon group which may have substituent(s) selected from the group consisting of a halogen atom, a lower alkyl group, an oxo group, a lower hydroxyalkyl group which may be protected and a lower alkoxy group or a group represented by $—A^{1ap}—W^{1p}—A^{1bp}—$ (wherein $A^{1ap}$ is a $C_{1-5}$ chain hydrocarbon group which may have substituent(s) selected from the group consisting of a halogen atom, a lower alkyl group, an oxo group, a lower hydroxyalkyl group which may be protected and a lower alkoxy group; $A^{1bp}$ is a single bond or a $C_{1-4}$ chain hydrocarbon group which may have substituent(s) selected from the group consisting of a halogen atom, a lower alkyl group, an oxo group, a lower hydroxyalkyl group which may be protected and a lower alkoxy group; $W^{1p}$ is an oxygen atom, a sulfur atom, an ethynylene group, a cyclopropylene group or a group represented by $—NR^{Wp}—$; and $R^{Wp}$ is a hydrogen atom, a lower alkyl group or a protecting group for an imino group); each of $X^p$ and $Y^p$ which are the same or different, is an oxygen atom, a sulfur atom, a carbonyl group or a group represented by $—CHR^a—$ (wherein $R^a$ is a hydrogen atom or a lower alkyl group) or $—NR^{bp}—$ (wherein $R^{bp}$ is a hydrogen atom, a lower alkyl group or an imino-protecting group), or $X^p$ and $Y^p$ together represent a vinylene group or an ethynylene group; each of $R^{1p}$, $R^{2p}$, $R^{3p}$, $R^{7p}$ and $R^{8p}$ which are the same or different, is a hydrogen atom, a halogen atom, a hydroxyl group which may be protected, a lower alkyl group, a lower alkenyl group or a lower alkoxy group; each of $R^{4p}$ and $R^{5p}$ which are the same or different, is a hydrogen atom, a halogen atom, a nitro group, a cyano group, a lower alkoxycarbonyl group, a carbamoyl group, a lower alkylcarbamoyl group, a lower alkyl group, a lower fluoroalkyl group, a lower alkoxy group, or a hydroxyl, amino, carboxyl or lower hydroxyalkyl group which may be protected; and $R^6$ is a lower alkyl group, provided that when one of $X^p$ and $Y^p$ is an oxygen atom, a sulfur atom or a group represented by $—NR^{bp}—$ (wherein $R^{bp}$ is the same as defined above), the other is a carbonyl group or a group represented by $—CHR^a—$ (wherein $R^a$ is the same as defined above), with a carboxylic acid represented by general formula (III) or its reactive derivative:

[wherein $A^{2p}$ is a $C_{2-8}$ chain hydrocarbon group which may have substituent(s) selected from the group consisting of a halogen atom, a lower alkyl group, a lower alkoxy group, a lower alkoxycarbonyl group, a lower alkenyloxycarbonyl group, an aryl group, an aralkyl group, and hydroxyl, lower hydroxyalkyl, carboxyl and lower carboxyalkyl groups which may be protected; and $R^p$ is a hydrogen atom or a carboxyl-protecting group] to obtain a compound represented by general formula (IV):

[IV]

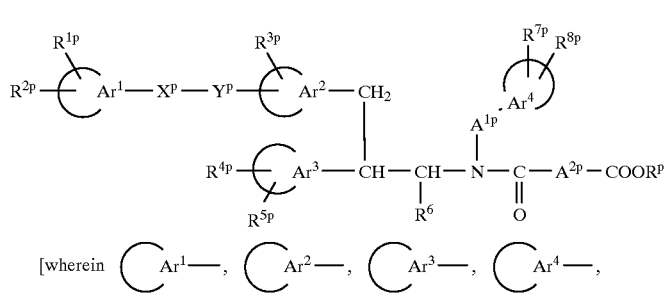

[wherein ⌬Ar¹—, ⌬Ar²—, ⌬Ar³—, ⌬Ar⁴—, $A^{1p}$, $A^{2p}$, $X^p$, $Y^p$, $R^{1p}$, $R^{2p}$, $R^{3p}$, $R^{4p}$, $R^{5p}$, $R^6$, $R^{7p}$, $R^{8p}$ and $R^p$ are the same as defined above] and, if necessary, removing any protecting group.

As the reactive derivative of the carboxylic acid represented by general formula (III), an acid halide, a mixed acid anhydride, an active ester or an active amide may, for example, be used.

When the carboxylic acid represented by general formula (III) is used, it is preferred to conduct the reaction in the presence of a condensing agent such as N,N'-dicyclohexylcarbodiimide, 1-ethyl-3-(3-dimethylaminopropyl)carbodiimide or 2-chloro-1,3-dimethylimidazolyl chloride.

The reaction of the compound represented by general formula (II) with the carboxylic acid represented by general formula (III) or its reactive derivative, is conducted usually by using 1 mol or an excess molar amount, preferably from 1 to 5 mols, of the carboxylic acid represented by general formula (III) or its reactive derivative, per mol of the compound represented by general formula (II).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 100° C.

The reaction time is usually from 5 minutes to 7 days, preferably from 10 minutes to 24 hours.

The above reaction can be conducted in the presence of a base to facilitate the reaction.

As such a base, it is preferred to conduct the reaction in the presence of an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine, 4-dimethylaminopyridine or N,N-dimethylaniline.

Such a base is used usually in an amount of 1 mol or an excess molar amount, preferably from 1 to 5 mols, per mol of the reactive derivative of the carboxylic acid represented by general formula (III).

The acid halide of the compound represented by general formula (III) can be obtained by reacting the carboxylic acid represented by general formula (III) with a halogenating agent in accordance with a conventional method. As the halogenating agent, thionyl chloride, phosphorus trichloride, phosphorus pentachloride, phosphorus oxychloride, phosphorus tribromide, oxalyl chloride or phosgene may, for example, be used.

The mixed acid anhydride of the compound represented by general formula (III) can be obtained by reacting the carboxylic acid represented by general formula (III) with an alkyl chlorocarbonate such as ethyl chlorocarbonate or with an aliphatic carboxylic acid chloride such as acetyl chloride, in accordance with a conventional method. Further, an intramolecular acid anhydride may be formed between carboxyl groups at both terminals, or when in general formula (III), a carboxyl group is present on the chain hydrocarbon group represented as $A^{2p}$, an intramolecular acid anhydride may be formed between such a carboxyl group and a carboxyl group to be involved in the reaction, to constitute a reactive derivative of the carboxylic acid.

The active ester of the compound represented by general formula (III) can be prepared by reacting the carboxylic acid represented by general formula (III) with an N-hydroxy compound such as N-hydroxysuccinimide, N-hydroxyphthalimide or 1-hydroxybenzotriazole, or a phenol compound such as a 4-nitrophenol, 2,4-dinitrophenol, 2,4,5-trichlorophenol or pentachlorophenol, in the presence of a condensing agent such as N,N'-dicyclohexylcarbodiimide or 1-ethyl-3-(3-dimethylaminopropyl)carbodiimide in accordance with a conventional method.

The active amide of the compound represented by general formula (III) can be prepared by reacting the carboxylic acid represented by general formula (III) with e.g. 1,1'-carbonyldiimidazole or 1,1'-carbonylbis(2-methylimidazole) in accordance with a conventional method.

When a hydroxyl group is present on the group represented by

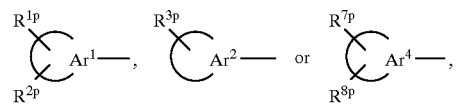

when a lower hydroxyalkyl group is present on the group represented by $A^{1p}$, when a hydroxyl group, a lower hydroxyalkyl group, a carboxyl group or a lower carboxyalkyl group is present on the group represented by $A^{2p}$, and when a hydroxyl group, an amino group, a carboxyl group or a lower hydroxyalkyl group is present on the group represented by

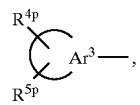

it is preferred to conduct the reaction after protecting such a hydroxyl group, a lower hydroxyalkyl group, an amino group, a carboxyl group or a lower carboxyalkyl group appropriately by a hydroxyl-protecting group, an amino-protecting group or a carboxyl-protecting group and remove the protecting group after the reaction. Further, in a case where one of $X^p$ and $Y^p$ is a group represented by $-NR^{bp}-$ (wherein $R^{bp}$ is the same as defined above), and the other is a group represented by $-CHR^a-$ (wherein $R^a$ is the same as defined above), $R^{bp}$ is preferably a lower alkyl group or an imino-protecting group, and when $R^{bp}$ is an imino-protecting group, it is preferred to remove such a protecting group after the reaction.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a p-nitrobenzyl group or a trityl group; or an acyl group such as a formyl group or an acetyl group. Particularly preferred is a methoxymethyl group, a tetrahydropyranyl group, a trityl group, a tert-butyldimethylsilyl group or an acetyl group.

The amino- or imino-protecting group may, for example, be an aralkyl group such as a benzyl group, a p-methoxybenzyl group, a p-nitrobenzyl group, a benzhydryl group or a trityl group; a lower alkanoyl group such as a formyl group, an acetyl group, a propionyl group, a butyryl group or a pivaloyl group; a lower haloalkanoyl group such as a trifluoroacetyl group; a lower alkoxycarbonyl group such as a methoxycarbonyl group, an ethoxycarbonyl group, a propoxycarbonyl group or a tert-butoxycarbonyl group; a lower haloalkoxycarbonyl group such as a 2,2,2-trichloroethoxycarbonyl group; an alkenyloxycarbonyl group such as a 2-propenyloxycarbonyl group; an aralkyloxycarbonyl group such as a benzyloxycarbonyl group or a p-nitrobenzyloxycarbonyl group; or a lower alkylsilyl group such as a trimethylsilyl group or a tert-butyldimethylsilyl group. Further, the amino-protecting group may, for example, be an aralkylidene group such as a benzylidene group, a p-chlorobenzylidene group or a p-nitrobenzylidene group. Particularly preferred is an acetyl group, a trifluoroacetyl group, a tert-butoxycarbonyl group or a benzyloxycarbonyl group.

The carboxyl-protecting group may, for example, be a lower alkyl group such as a methyl group, an ethyl group, a propyl group, an isopropyl group or a tert-butyl group; a lower haloalkyl group such as a 2,2,2-trichloroethyl group; a lower alkenyl group such as 2-propenyl group; or an aralkyl group such as a benzyl group, a p-methoxybenzyl group, a p-nitrobenzyl group, a benzhydryl group or trityl group. Particularly preferred is a methyl group, an ethyl group, a tert-butyl group, a 2-propenyl group, a benzyl group, a p-methoxybenzyl group or a benzhydryl group.

After completion of the reaction, conventional treatment is conducted to obtain a crude product of the compound represented by general formula (IV). The compound represented by general formula (IV) may or may not be purified in accordance with a conventional method, and if necessary, reactions for removing protecting groups for a hydroxyl group, an amino group and a carboxyl group may be carried out in a proper combination to obtain a compound of the formula (I).

Removal of protecting groups may vary depending upon their types, but can be conducted in accordance with the methods disclosed in literature (Protective Groups in Organic Synthesis, T. W. Greene, John Wiley & Sons (1981)) or methods similar thereto, for example by solvolysis employing an acid or a base, by chemical reduction employing a metal hydride complex or by catalytic reduction employing a palladium-carbon catalyst or Raney nickel.

Process 2

A compound represented by general formula (I-a):

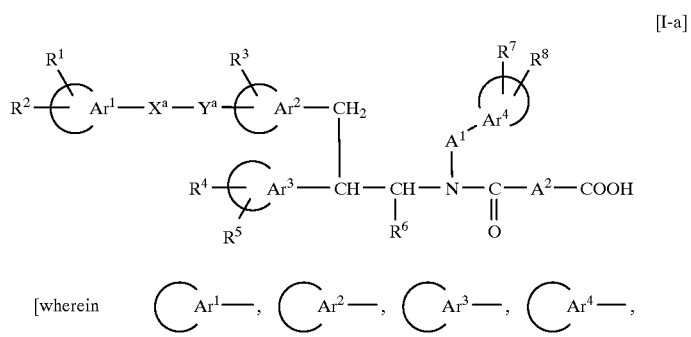

[wherein $A^1$, $A^2$, $R^1$, $R^2$, $R^3$, $R^4$, $R^5$, $R^6$, $R^7$ and $R^8$ are the same as defined above; and X and Y are the same as defined below] can be prepared by reacting a compound represented by general formula (V):

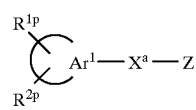

[wherein $X^a$ is a carbonyl group or a group represented by $-CHR^a-$ (wherein $R^a$ is the same as defined above); Z is a leaving group; and

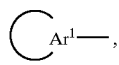

$R^{1p}$ and $R^{2p}$ are the same as defined above] with a compound represented by general formula (VI):

[VI]

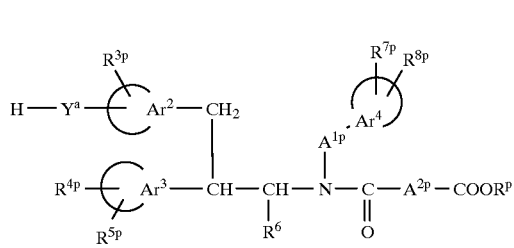

[wherein $Y^a$ is an oxygen atom, a sulfur atom or a group represented by —$NR^b$— (wherein $R^b$ is the same as defined above); and

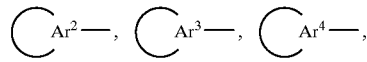

$A^{1p}$, $A^{2p}$, $R^{3p}$, $R^{4p}$, $R^{5p}$, $R^6$, $R^{7p}$, $R^{8p}$ and $R^p$ are the same as defined above] to obtain a compound represented by general formula (IV-a):

[IV-a]

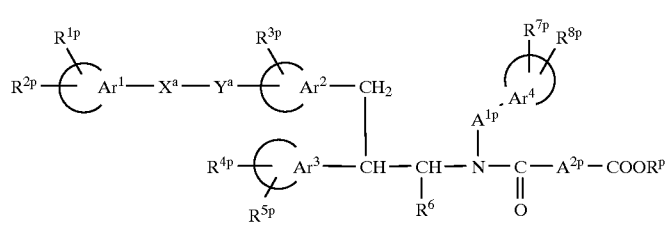

[wherein

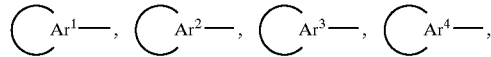

$A^{1p}$, $A^{2p}$, $X^a$, $Y^a R^{1p}$, $R^{2p}$, $R^{3p}$, $R^{4p}$, $R^{5p}$, $R^6$, $R^{7p}$, $R^{8p}$ and $R^p$ are the same as defined above] and, if necessary, removing any protecting group.

Process 2 is a process for preparing a compound represented by general formula (I) wherein —X—Y— is a group represented by —COO—, —COS—, —CONR$^b$—, —CHR$^a$O—, —CHR$^a$S— or —CHR$^a$NR$^b$— (wherein R$^a$ and R$^b$ are the same as defined above) i.e. a compound represented by general formula (I-a).

The reaction of a compound represented by general formula (V) with a compound represented by general formula (VI) is carried out usually by using 1 mol or an excess molar amount, preferably from 1 to 3 mols, of the compound represented by general formula (V), per mol of the compound represented by general formula (VI).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 100° C.

The reaction time is usually from 5 minutes to 7 days, preferably from 10 minutes to 24 hours.

The above reaction is preferably conducted in the presence of a base to facilitate the reaction. Especially when $Y^a$ in general formula (VI) is not a group represented by —$NR^b$—, it is necessary to carry out the reaction in the presence of an inorganic base such as sodium hydride, n-butyllithium, sodium hydroxide, potassium hydroxide, calcium hydroxide, sodium carbonate, potassium carbonate or sodium hydrogencarbonate, or an organic base such as triethylamine, N-ethyldiisopropylamine, pyridine, 4-dimethylaminopyridine or N,N-dimethylaniline.

The base is used usually in an amount of 1 mol or an excess molar amount, preferably from 1 to 5 mols, per mol of the compound represented by general formula (V).

The leaving group represented by Z in general formula (V) may, for example, be a halogen atom such as a chlorine atom, a bromine atom or an iodine atom, or an organic sulfonyloxy group such as a methanesulfonyloxy group, a p-toluenesulfonyloxy group or a benzenesulfonyloxy group.

When a hydroxyl group is present on the group represented by

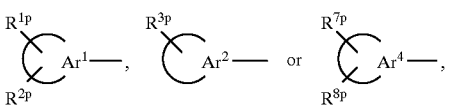

when a lower hydroxyalkyl group is present on the group represented by $A^{1p}$, when a hydroxyl group, a lower hydroxyalkyl group, a carboxyl group or a lower carboxyalkyl group is present on the group represented by $A^{2p}$, and when a hydroxyl group, an amino group, a carboxyl group or a lower hydroxyalkyl group is present on the group represented by

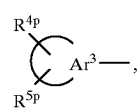

it is preferred to conduct the reaction after protecting such a hydroxyl group, a lower hydroxyalkyl group, an amino group, a carboxyl group or a lower carboxyalkyl group appropriately by a hydroxyl-protecting group, an amino-protecting group or a carboxyl-protecting group and remove any protecting group after the reaction.

The hydroxyl-protecting group, the amino-protecting group and the carboxyl-protecting group may be the protecting groups mentioned above with respect to process 1.

After completion of the reaction, usual treatment is carried out to obtain a crude product of the compound represented by general formula (IV-a). The compound represented by general formula (IV-a) thus obtained may or may not be purified by a conventional method, and if necessary, reactions for removing the hydroxyl-, amino- and carboxyl-protecting groups may be carried out in a proper combination to obtain a compound represented by general formula (I-a).

The method for removing a protecting group varies depending upon the type of the protecting group and the stability of the desired compound (I-a). However, removal of protecting groups can be appropriately conducted in accordance with the methods disclosed in the above-mentioned literature or methods similar thereto.

Process 3

A compound represented by general formula (I-b):

[I-b]

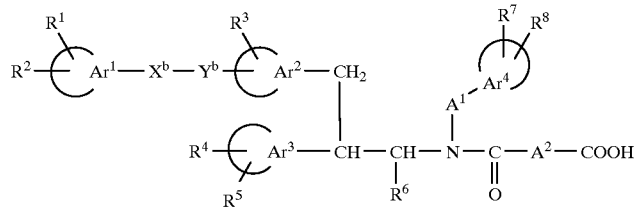

[wherein

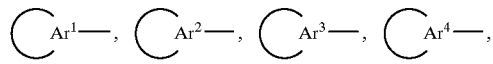

$A^1$, $A^2$, $R^1$, $R^2$, $R^3$, $R^4$, $R^5$, $R^6$, $R^7$ and $R^8$ are the same as defined above, and $X^a$ and $Y^b$ are the same as defined below] can be prepared by reacting a compound represented by general formula (VII):

[VII]

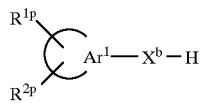

[wherein $X^b$ is an oxygen atom, a sulfur atom or a group represented by —$NR^b$— (wherein $R^b$ is the same as defined above); and

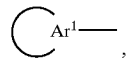

$R^{1p}$ and $R^{2p}$ are the same as defined above] with a compound represented by general formula (VIII):

[VIII]

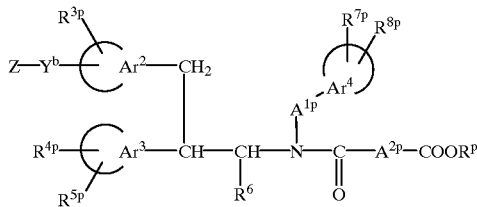

[wherein $Y^b$ is a carbonyl group or a group represented by —$CHR^a$— (wherein $R^a$ is the same as defined above); and

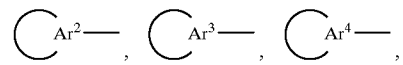

$A^{1p}$, $A^{2p}$, Z, $R^{3p}$, $R^{4p}$, $R^{5p}$, $R^6$, $R^{7p}$, $R^{8p}$ and $R^p$ are the same as defined above] to obtain a compound represented by general formula (IV-b):

[IV-b]

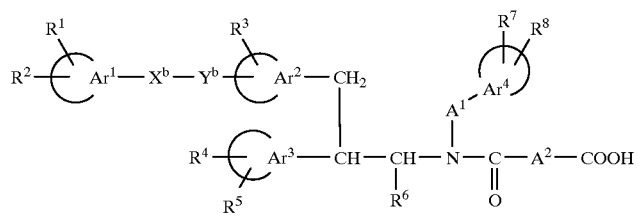

[wherein

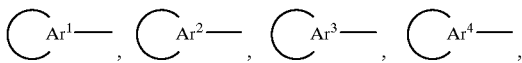

$A^{1p}$, $A^{2p}$, $X^b$, $Y^b$, $R^{1p}$, $R^{2p}$, $R^{3p}$, $R^{4p}$, $R^{5p}$, $R^6$, $R^{7p}$, $R^{8p}$ and $R^p$ are the same as defined above] and, if necessary, removing any protecting group.

Process 3 is a process for preparing a compound represented by general formula (I) wherein —X—Y— is a group represented by —OCO—, —SCO—, —$NR^b$CO—, —$OCHR^a$—, —$SCHR^a$— or —$NR^bCHR^a$— (wherein $R^a$ and $R^b$ are the same as defined above) i.e. a compound represented by general formula (I-b).

This process can be conducted usually in an inert solvent, preferably in the presence of a base, by using 1 mol or an excess molar amount, preferably from 1 to 3 mols, of the compound represented by general formula (VII), per mol of the compound represented by general formula (VIII). The types of the inert solvent and the base as well as the reaction conditions may be the same as described above with respect to process 2. Accordingly, the reaction and the post-treatment after the reaction may preferably be carried out all in accordance with process 2.

Further, in the above processes 2 and 3, when $X^a$ or $Y^b$ is a carbonyl group, a compound wherein the group corresponding to Z is a hydroxyl group i.e. a compound wherein Z and the adjacent $X^a$ or $Y^b$ together represent a carboxyl group, can be used. In such a case, the reaction conditions, etc. are preferably in accordance with the reaction conditions for the reaction of the compound represented by general formula (II) with the compound represented by general formula (III) in the above process 1.

Process 4

A compound represented by general formula (I-c):

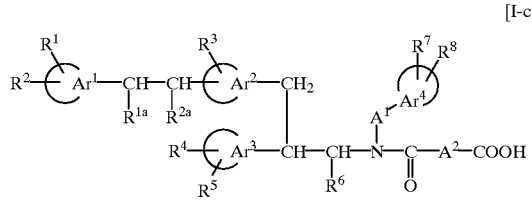
[I-c]

[wherein

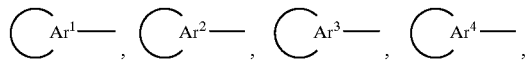

$A^1$, $A^2$, $R^1$, $R^2$, $R^3$, $R^4$, $R^5$, $R^6$, $R^7$ and $R^8$ are the same as defined above, and $R^{1a}$ and $R^{2a}$ are the same as defined below] can be prepared by reacting a compound represented by general formula (IX):

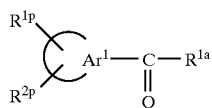
[IX]

[wherein $R^{1a}$ is a hydrogen atom or a lower alkyl group; and

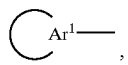

$R^{1p}$ and $R^{2p}$ are the same as defined above] with a compound represented by general formula (X):

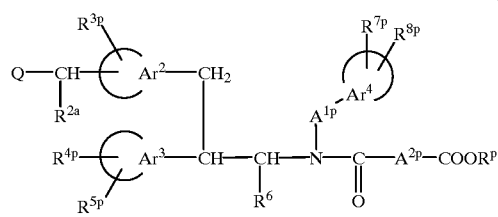
[X]

[wherein Q is a triphenylphosphonio group, a dimethoxyphosphoryl group or a diethoxyphosphoryl group; $R^{2a}$ is a hydrogen atom or a lower alkyl group; and

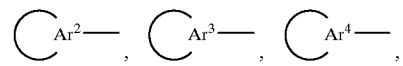

$A^{1p}$, $A^{2p}$, $R^{3p}$, $R^{4p}$, $R^{5p}$, $R^6$, $R^{7p}$, $R^{8p}$ and $R^p$ are the same as defined above] to obtain a compound represented by general formula (XI):

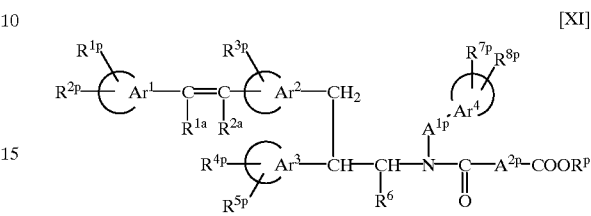
[XI]

[wherein

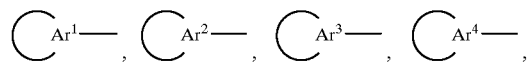

$A^{1p}$, $A^{2p}$, $R^{1p}$, $R^{2p}$, $R^{3p}$, $R^{4p}$, $R^{5p}$, $R^6$, $R^{7p}$, $R^{8p}$, $R^p$, $R^{1a}$ and $R^{2a}$ are the same as defined above] then reducing the compound represented by general formula (XI), and, if necessary, removing any protecting group.

Process 4 is a process for preparing a compound represented by general formula (I) wherein —X—Y— is a group represented by —CHR$^{1a}$CHR$^{2a}$— (wherein each of R$^{1a}$ and R$^{2a}$ which are the same or different, is a hydrogen atom or a lower alkyl group) i.e. a compound represented by general formula (I-c).

The reaction of the compound represented by general formula (IX) with the compound represented by general formula (X) is carried out usually by employing equimolar amounts of the two reactants or using a slightly excess amount of one of them.

The reaction is carried out usually in an inert solvent. Such an inert solvent may, for example, be an ether such as ethyl ether, tetrahydrofuran or dioxane; an aromatic hydrocarbon such as benzene, toluene, chlorobenzene or xylene; an aprotic polar solvent such as dimethylformamide, ethyl acetate or hexamethylphosphoric triamide; or a mixture of such solvents.

The reaction temperature is usually from —100° C. to the boiling point of the solvent used for the reaction, preferably from −70° C. to 50° C.

The reaction time is usually from 5 minutes to 7 days, preferably from 10 minutes to 24 hours.

Further, the above reaction is preferably conducted in the presence of a base such as sodium hydride, n-butyllithium, sodium methoxide, potassium tert-butoxide, sodium hydroxide or potassium hydroxide.

Such a base is used in an amount of 1 mol or an excess molar amount, preferably from 1 to 5 mols per mol of the compound represented by general formula (X).

The reaction of reducing the compound represented by general formula (XI) obtained in the above step is usually preferably conducted by catalytic reduction employing a palladium-carbon catalyst, a Raney nickel catalyst or a platinum catalyst in an inert solvent.

The inert solvent may, for example, be an alcohol such as methanol, ethanol or propanol, or acetic acid.

The reaction temperature is usually from −20° C. to 100° C., preferably from 0° C. to room temperature.

The reaction time is usually from 5 minutes to 7 days, preferably from 10 minutes to 24 hours.

The hydrogen pressure in the catalytic reduction reaction is usually preferably from atmospheric pressure to 5 atm, and the amount of the catalyst is usually from 0.01 to 1 mol, preferably from 0.05 to 0.2 mol, per mol of the starting material compound (XI).

After completion of the reaction, the product is subjected to usual treatment after removing any protecting group if such a protecting group is present or directly if no such protecting group is present, to obtain a compound represented by general formula (I-c).

Removal of the protecting group and the post treatment may be conducted by the methods described with respect to the above process 1.

Process 5

A compound represented by general formula (I-c):

[I-c]

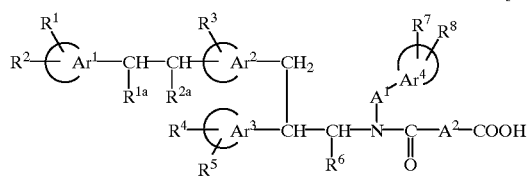

[wherein

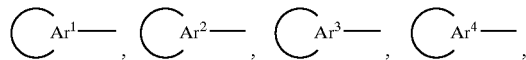

$A^1, A^2, R^1, R^2, R^3, R^4, R^5, R^6, R^7, R^8, R^{1a}$ and $R^{2a}$ are the same as defined above] can be obtained by reacting a compound represented by general formula (XII):

[XII]

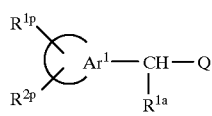

[wherein

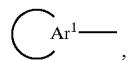

Q, $R^{1p}$, $R^{2p}$ and $R^{1a}$ are the same as defined above] with a compound represented by general formula (XIII):

[VIII]

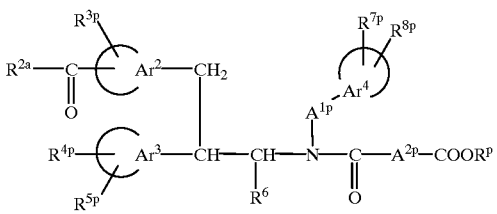

[wherein

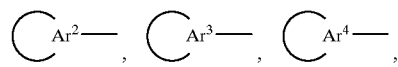

$A^{1p}$, $A^{2p}$, $R^{3p}$, $R^{4p}$, $R^{5p}$, $R^6$, $R^{7p}$, $R^{8p}$, $R^p$ and $R^{2a}$ are the same as defined above] to obtain a compound represented by general formula (XI):

[XI]

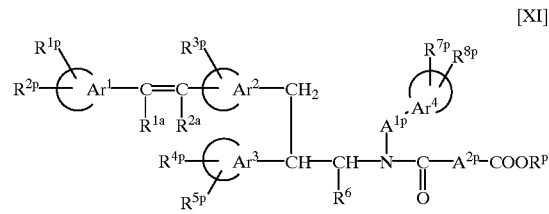

[wherein

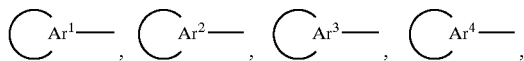

$A^{1p}$, $A^{2p}$, $R^{1p}$, $R^{2p}$, $R^{3p}$, $R^{4p}$, $R^{5p}$, $R^6$, $R^{7p}$, $R^{8p}$, $R^p$, $R^{1a}$ and $R^{2a}$ are the same as defined above] then reducing the compound represented by general formula (XI), and, if necessary, removing any protecting group.

Like process 4, process 5 is a process for producing a compound represented by general formula (I) wherein —X—Y— is a group represented by —CHR$^{1a}$CHR$^{2a}$— (wherein R$^{1a}$ and R$^{2a}$ are the same as defined above) i.e. a compound represented by general formula (I-c).

Process 5 is equal to the reaction of process 4 wherein the staring material compounds (IX) and (X) are replaced by compounds (XIII) and (XII), respectively. Accordingly, the manner and conditions of the reaction may be all in accordance with process 4.

Further, a compound represented by general formula (I-d):

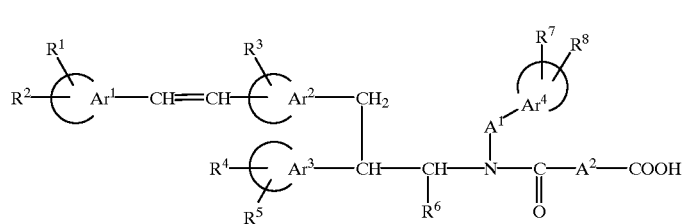

[I-d]

[wherein

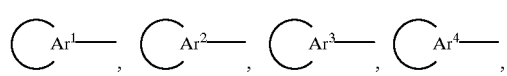

$A^1$, $A^2$, $R^1$, $R^2$, $R^3$, $R^4$, $R^5$, $R^6$, $R^7$ and $R^8$ are the same as defined above] can be obtained by removing a protecting group, as the case requires, from a compound represented by general formula (XI-a):

[wherein

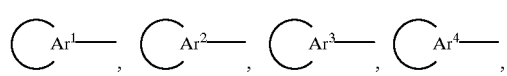

$A^1$, X, Y, $R^1$, $R^2$, $R^3$, $R^4$, $R^5$, $R^6$, $R^7$, $R^8$, $R^{11}$, $R^{12}$, p, q and r are the same as defined above] can be prepared by oxidizing a compound represented by general formula (IV-e):

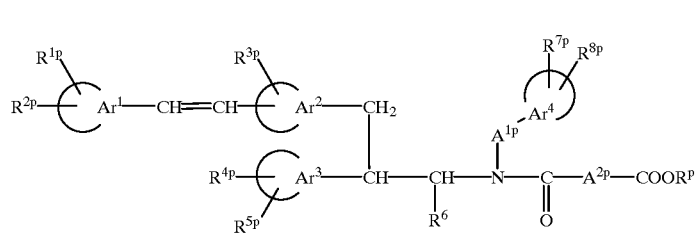

[XI-a]

[wherein

$A^{1p}$, $A^{2p}$, $R^{1p}$, $R^{2p}$, $R^{3p}$, $R^{4p}$, $R^{5p}$, $R^6$, $R^{7p}$, $R^{8p}$ and $R^p$ are the same as defined above] i.e. a compound represented by general formula (XI) wherein both $R^{1a}$ and $R^{2a}$ are hydrogen atoms, among compounds represented by general formula (XI) obtainable as intermediates in the above processes 4 and 5.

Process 6

A compound represented by general formula (I-e):

[I-e]

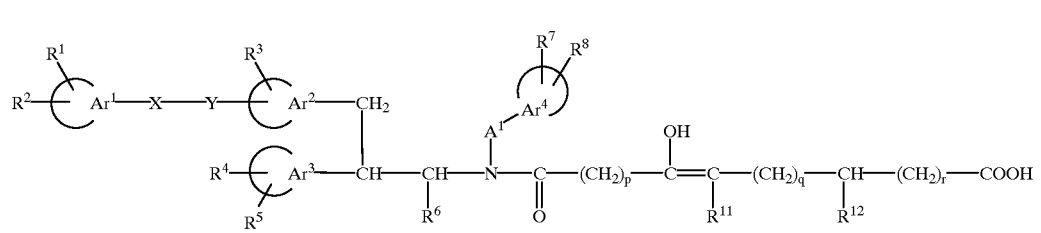

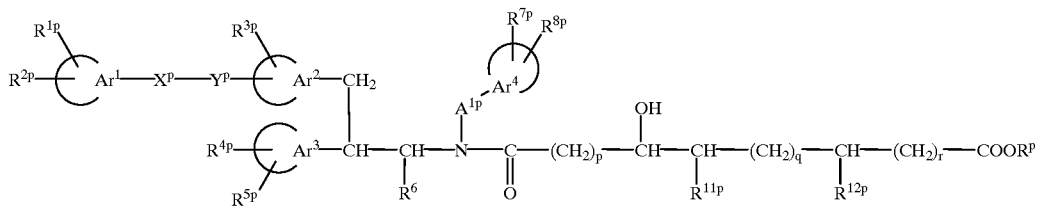

[IV-e]

[wherein $R^{11p}$ is a hydrogen atom, a lower alkoxycarbonyl group or a lower alkenyloxycarbonyl group or a lower hydroxyalkyl or carboxyl group which may be protected, $R^{12p}$ is a hydrogen atom or a hydroxyl or carboxyl group which may be protected; and

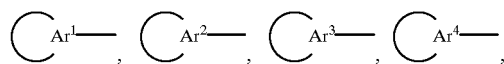

$A^{1p}$, $X^p$, $Y^p$, $R^{1p}$, $R^{2p}$, $R^{3p}$, $R^{4p}$, $R^{5p}$, $R^6$, $R^{7p}$, $R^{8p}$, $R^p$, p, q and r are the same as defined above] and, if necessary, removing any protecting group.

Process 6 is a process for preparing a compound represented by general formula (I) wherein $A^2$ is a group represented by formula (b):

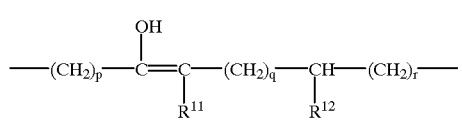

[b]

[wherein $R^{11}$, $R^{12}$, p, q and r are the same as defined above], i.e. a compound represented by general formula (I-e).

The reaction of oxidizing the compound represented by general formula (IV-e) is usually preferably carried out in an inert solvent by using so-called Dess-Martin oxidation employing 12-I-5 triacetoxyperiodinane; so-called Swern oxidation employing oxalyl chloride and dimethyl sulfoxide; a sulfur trioxide-pyridine complex; pyridinium chlorochromate; active manganese dioxide; or tetra-n-propylammonium perruthenate.

The inert solvent may, for example, be a halogenated hydrocarbon such as methylene chloride, chloroform or dichloroethane; an ether such as ethyl ether, tetrahydrofuran or dioxane; an aprotic polar solvent such as acetonitrile, acetone, ethyl acetate or dimethyl sulfoxide; or a mixture of such solvents.

The reaction temperature varies depending upon the type of the oxidizing agent to be used, etc. However, it is usually from −100° C. to the boiling point of the solvent used for the reaction, preferably from −70° C. to 100° C.

The reaction time is usually from 5 minutes to 7 days, preferably from 10 minutes to 24 hours.

After completion of the reaction, the product is subjected to usual treatment after removing a protecting group when such a protecting group is present, or directly when no such protecting group is present, to obtain the compound represented by general formula (I-e).

The removal of the protecting group and the post-treatment may be conducted in the same manner as described above with respect to process 1.

Further, a compound corresponding to the compound represented by general formula (IV-e) to be used as the starting material in the above process 6, can be prepared, for example, by hydrolyzing a compound represented by general formula (IV-e-1):

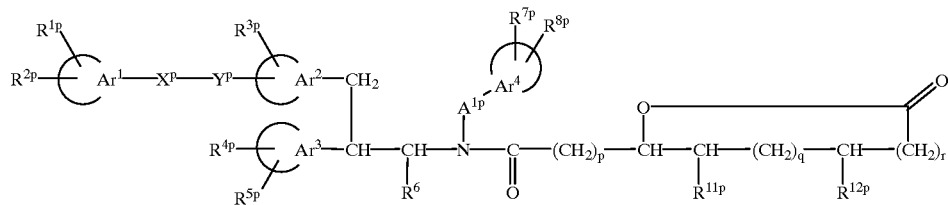

[IV-e-1]

[wherein

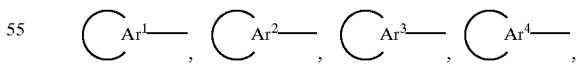

$A^{1p}$, $X^p$, $Y^p$, $R^{1p}$, $R^{2p}$, $R^{3p}$, $R^{4p}$, $R^{5p}$, $R^6$, $R^{7p}$, $R^{8p}$, $R^{11p}$, $R^{12p}$, p, q and r are the same as defined above] in the presence of a base, to obtain a compound represented by general formula (IV-e-2):

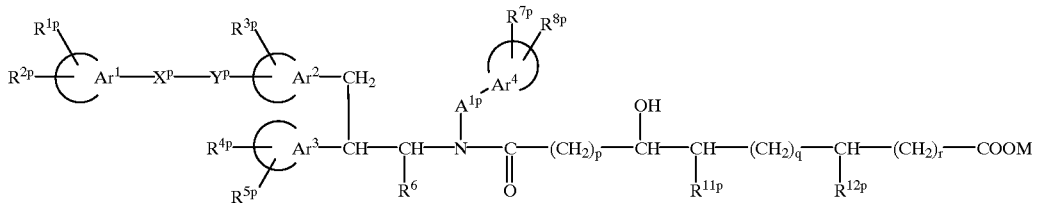

[IV-e-2]

[wherein M is a hydrogen atom or an alkali metal atom; and

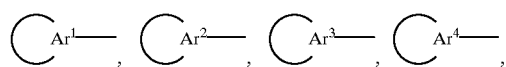

$A^{1p}$, $X^p$, $Y^p$, $R^{1p}$, $R^{2p}$, $R^{3p}$, $R^{4p}$, $R^{5p}$, $R^6$, $R^{7p}$, $R^{8p}$, $R^{11p}$, $R^{12p}$, p, q and r are the same as defined above] then reacting thereto a diazo compound represented by the general formula

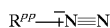

(wherein $R^{pp}$ is a lower alkyl group, a lower alkenyl group, an aralkyl group or a lower alkoxycarbonylalkyl group) or an alkylating agent represented by the general formula $R^{pp}$—$Z^1$ (wherein $R^{pp}$ and $Z^1$ are the same as defined above).

Isolation and purification of the compound represented by general formula (I), (I-a), (I-b), (I-c), (I-d) or (I-e), obtained by the above process can be conducted by a single use or a proper combination of conventional separating means such as column chromatography employing silica gel, adsorbent resin, etc., liquid chromatography, solvent extraction and recrystallization-reprecipitation.

The compound represented by general formula (I), (I-a), (I-b), (I-c), (I-d) or (I-e) can be converted to a pharmaceutically acceptable salt or ester by a conventional method. Reversely, the conversion from the salt or ester to a free carboxylic acid can also be conducted by a conventional method.

The compounds represented by general formulas (II), (III), (V), (VI), (VII), (VIII), (IX), (X), (XII) and (XIII) may be commercially available or can be prepared in accordance with the methods disclosed in literature (J. Med. Chem., 10, 717 (1967); ibid., 725; Chem. Lett., 191 (1980); ibid., 93 (1982); ibid., 375 (1984); J. Chem. Soc. Chem. Commun., 579 (1984); Tetrahedron Letters, 36, 7459 (1995)) or methods similar thereto, or in accordance with the following processes or the methods disclosed in Reference Examples.

Process A

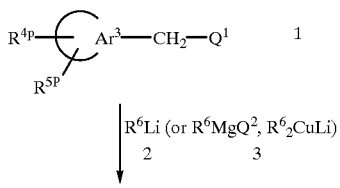

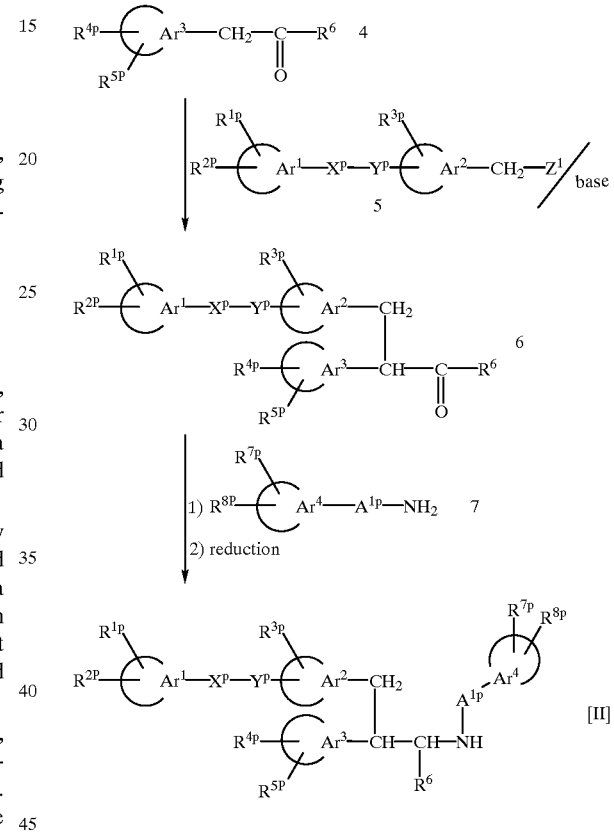

[wherein $Q^1$ is a cyano group, a carboxyl group, a lower alkoxycarbonyl group, a chloroformyl group or an N-methoxy-N-methylcarbamoyl group; $Q^2$ is a halogen atom; $Z^1$ is a leaving group selected from the group consisting of a chlorine atom, a bromine atom, an iodine atom, a trifluoroacetoxy group, a methanesulfonyloxy group, a trifluoromethanesulfonyloxy group and a p-toluenesulfonyloxy group; and

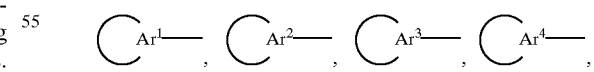

$A^{1p}$, $X^p$, $Y^p$, $R^{1p}$, $R^{2p}$, $R^{3p}$, $R^{4p}$, $R^{5p}$, $R^6$, $R^{7p}$ and $R^{8p}$ are the same as defined above]

By this process, desired compound (II) can be prepared by reacting a nitrile or a carboxylic acid derivative represented by general formula 1 with an alkyllithium represented by general formula 2 or an alkyl Grignard reagent (or an alkyl Gilman reagent) represented by general formula 3 to obtain a ketone compound 4, then reacting an alkylating agent represented by general formula 5 to the ketone compound 4 to produce a compound represented by general formula 6, then reacting the compound 6 with an amine compound represented by general formula 7, followed by reduction.

The above reaction steps will be described in detail referring to suitable reaction conditions, etc.

The first step of preparing the ketone compound 4 is conducted usually by reacting 1 mol or an excess molar amount, preferably from 1 to 5 mols of the alkyllithium reagent 2 or the alkyl Grignard reagent (or the alkyl Gilman reagent in the case where the substituent $Q^1$ of the compound 1 is a chloroformyl group) 3 to 1 mol of the starting material compound 1 in a solvent inert to the reaction such as tetrahydrofuran, ethyl ether or benzene, if necessary followed by hydrolysis under an acidic condition.

The reaction temperature is usually from −80° C. to the boiling point of the solvent used for the reaction, preferably from −70° C. to 50° C. The reaction time is usually from 5 minutes to 48 hours, preferably from 30 minutes to 24 hours.

When the substituent $Q^1$ in the formula of the starting material compound 1 is a cyano group, it may be necessary to conduct a hydrolytic reaction under an acidic condition after completion of the reaction, and such a hydrolytic reaction is conducted in e.g. methanol, ethanol, tetrahydrofuran or a solvent mixture thereof with water in the presence of an acid such as hydrochloric acid, sulfuric acid or p-toluenesulfonic acid.

The reaction temperature is usually from 0° C. to the boiling point of the solvent used for the reaction, and the reaction time is from 30 minutes to 24 hours.

The step of preparing the compound represented by general formula 6 from the ketone compound 4, can be conducted by reacting 1 mol or an excess molar amount, preferably from 1 to 2 mols, of the alkylating agent represented by general formula 5 to the ketone compound 4 in the presence of a base in an inert solvent which does not adversely affect the reaction or without using any solvent.

The inert solvent may, for example, be an ether such as ethyl ether, tetrahydrofuran or dioxane; an aromatic hydrocarbon such as benzene, toluene or xylene; an aprotic polar solvent such as dimethylformamide, dimethyl sulfoxide or hexamethylphosphoric triamide, or a mixture of such solvents.

The base to be used for this reaction, may, for example, be an alkali metal hydride such as sodium hydride, lithium hydride or potassium hydride; a lithium amide such as lithium amide, lithium diisopropylamide or lithium bis(trimethylsilyl)amide; an alkyllithium such as methyllithium, butyllithium or tert-butyllithium; an alkali metal alkoxide such as sodium methoxide, sodium ethoxide or potassium tert-butoxide; or an alkali metal hydroxide such as sodium hydroxide, potassium hydroxide or lithium hydroxide.

The base is used usually in an amount of 1 mol or an excess molar amount, preferably from 1 to 5 mols, per mol of the starting material alkylating agent 5.

The reaction temperature is usually from −100° C. to the boiling point of the solvent used for the reaction, preferably from −80° C. to 100° C. The reaction time is usually from 10 minutes to 48 hours, preferably from 30 minutes to 24 hours.

The step of preparing the desired compound (II) from the compound represented by general formula 6 can be conducted usually in an inert solvent such as methanol, ethanol, benzene, ethyl ether or tetrahydrofuran by reacting 1 mol or an excess molar amount, preferably from 1 to 2 mols, of the amine compound represented by general formula 7 to 1 mol of the compound represented by general formula 6 to preliminarily form an imine, which is subsequently reduced.

The reaction temperature in the process for forming the above imine is usually from 0° C. to the boiling point of the solvent used for the reaction, preferably from room temperature to 100° C. The reaction time is usually from 5 minutes to 48 hours, preferably from 30 minutes to 24 hours. After the formation of the imine, the reaction solution may be used as it is to the subsequent step of the reduction reaction, or the reaction solution may be distilled or subjected to a conventional separation means to isolate the imine compound, which is then subjected to the subsequent reduction.

The reduction can be carried out by using a metal hydride complex such as sodium borohydride, sodium cyanoborohydride or lithium aluminum hydride, or by catalytic reduction employing a palladium-carbon catalyst or a Raney nickel catalyst.

When a metal hydride complex is used as a reducing agent, the reducing agent is used usually in an amount of 1 mol or an excess molar amount, preferably from 1 to 5 mols, per mol of the above imine.

For the reduction, an inert solvent, for example, an alcohol such as methanol or ethanol; an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene; or a mixture of such solvents, can be used appropriately as a solvent depending upon the type of the reducing agent.

The reaction temperature is usually from 0° C. to room temperature, and the reaction time is usually from 1 hour to 6 hours.

Further, in this process, it is also possible to react an alkylating agent represented by general formula 5 to the nitrile or carboxylic acid derivative represented by general formula 1 to preliminarily produce an alkyl compound and then to react an alkyllithium represented by general formula 2 or an alkyl Grignard reagent (or an alkyl Gilman reagent) represented by general formula 3 to the alkyl compound to obtain a compound represented by general formula 6. Such a reaction can be conducted under the conditions similar to Process A described above. Accordingly, the reaction conditions described above for Process A may all be used as the reaction conditions for this reaction.

The compounds represented by general formulas 1, 2, 3, 5 and 7 may be commercially available or can be produced by a proper combination, as the case requires, of the methods disclosed in Reference Examples, or conventional methods or methods similar thereto.

Process B

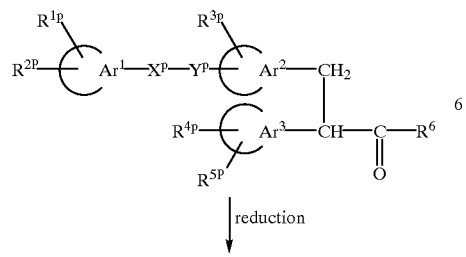

-continued

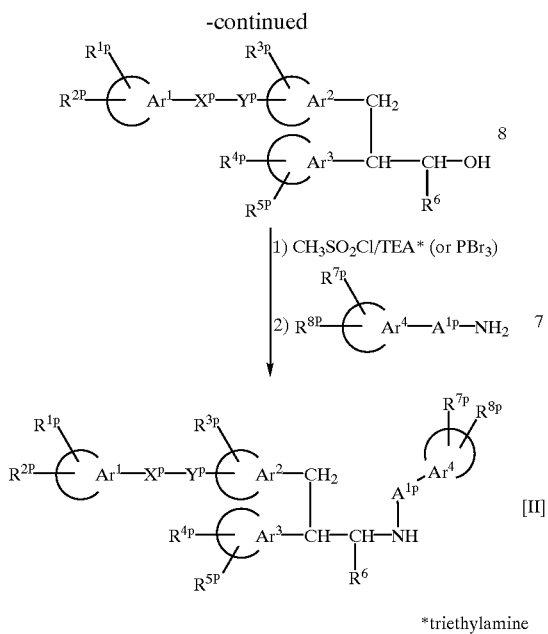

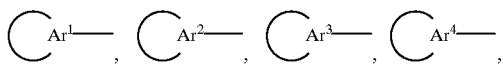

[wherein $$\underset{Ar^1-}{\bigcirc}, \underset{Ar^2-}{\bigcirc}, \underset{Ar^3-}{\bigcirc}, \underset{Ar^4-}{\bigcirc},$$

$A^{1p}, X^p, Y^p, R^{1p}, R^{2p}, R^{3p}, R^{5p}, R^6, R^{7p}$ and $R^{8p}$ are the same as defined above]

According to this process, the desired compound (II) can be prepared by reacting a reducing agent such as a metal hydride complex to a compound represented by general formula 6 to obtain an alcohol compound 8 and reacting an amine compound represented by general formula 7 to the alcohol compound 8.

The above reaction steps will be described in detail referring to suitable reaction conditions, etc.

The step of reducing the compound represented by general formula 6 to the alcohol compound 8 can be conducted usually by using a metal hydride complex such as sodium borohydride, diisobutyl aluminum hydride, lithium aluminum hydride or lithium tri-sec-butylborohydride (L-selectride™), or by catalytic reduction employing e.g. a palladium-carbon catalyst or a Raney nickel catalyst, in an inert solvent which does not adversely affect the reaction.

When the metal hydride complex is used as the reducing agent, such a reducing agent is used usually in an amount of 1 mol or an excess molar amount, preferably from 1 to 5 mols, per mol of the starting material compound 6.

The inert solvent to be used in this reaction may be suitably selected depending upon the type of the reducing agent.

For example, when the reducing agent is sodium borohydride, an inert solvent, such as an alcohol such as methanol or ethanol; an ether such as dimethoxyethane, dioxane, tetrahydrofuran or diglyme; an aprotic polar solvent such as dimethylformamide or dimethylacetamide, or water, or a solvent mixture thereof, may be used, and particularly preferred is an alcohol such as methanol or ethanol.

For example, when the reducing agent is diisobutylaluminum hydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; an aromatic hydrocarbon such as benzene or toluene; methylene chloride, or a solvent mixture thereof, may be used, and particularly preferred is toluene or methylene chloride.

For example, when the reducing agent is lithium aluminum hydride or lithium tri-sec-butylborohydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene, or a solvent mixture thereof, may be used, and particularly preferred is ethyl ether or tetrahydrofuran.

For the catalytic reduction, the solvent is preferably an alcohol such as methanol or ethanol.

The reaction temperature and the reaction time vary depending upon the stability and the susceptibility to the reduction reaction of the starting material ketone compound 6, the type of the reducing agent and the type of the solvent. However, the reaction temperature is usually from −80° C. to 100° C., preferably from −70° C. to 40° C., and the reaction time is usually from 5 minutes to 2 days, preferably from 30 minutes to 24 hours.

The step of preparing the desired compound (II) from a compound represented by general formula 8 can be carried out by reacting a sulfonating agent such as methanesulfonyl chloride to the alcohol compound represented by general formula 8 in the presence of a base, or reacting a halogenating agent such as thionyl chloride or phosphorus tribromide thereto, to convert the hydroxyl group in the formula to a leaving group, followed by reacting an amine compound represented by general formula 7.

The reaction for introducing the leaving group can be conducted usually by reacting 1 mol or excess molar amounts, preferably from 1 to 2 mols, of a sulfonating agent and a base such as triethylamine to 1 mol of the alcohol compound 8 in an inert solvent such as methylene chloride, chloroform, benzene, tetrahydrofuran or ethyl acetate, or using 1 mol or an excess molar amount, preferably from 1 to 5 mols, of a halogenating agent.

The reaction temperature is usually from −70° C. to the boiling point of the solvent used for the reaction, preferably from −20° C. to 80° C., and the reaction time is usually from 5 minutes to 48 hours, preferably from 30 minutes to 24 hours.

Then, the step of reacting an amine compound 7 to the compound having the leaving group introduced, obtained by the above reaction, can be conducted usually by employing 1 mol or an excess molar amount, preferably from 1 to 50 mols, of the amine compound 7 per mol of the starting compound having the leaving group, in an inert solvent such as methylene chloride, chloroform, benzene, ethyl ether or tetrahydrofuran.

If necessary, this reaction can be conducted in the presence of a base other than the amine compound represented by general formula 7.

As such a base, an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine or N,N-dimethylaniline may, for example, be mentioned.

Such a base is used usually in an amount of 1 mol or an excess molar amount, preferably from 1 to 5 mols, per mol of the starting material compound.

The reaction temperature is usually from −50° C. to 150° C., preferably from −20° C. to 100° C., and the reaction time is usually from 5 minutes to 7 days, preferably from 10 minutes to 24 hours.

Process C

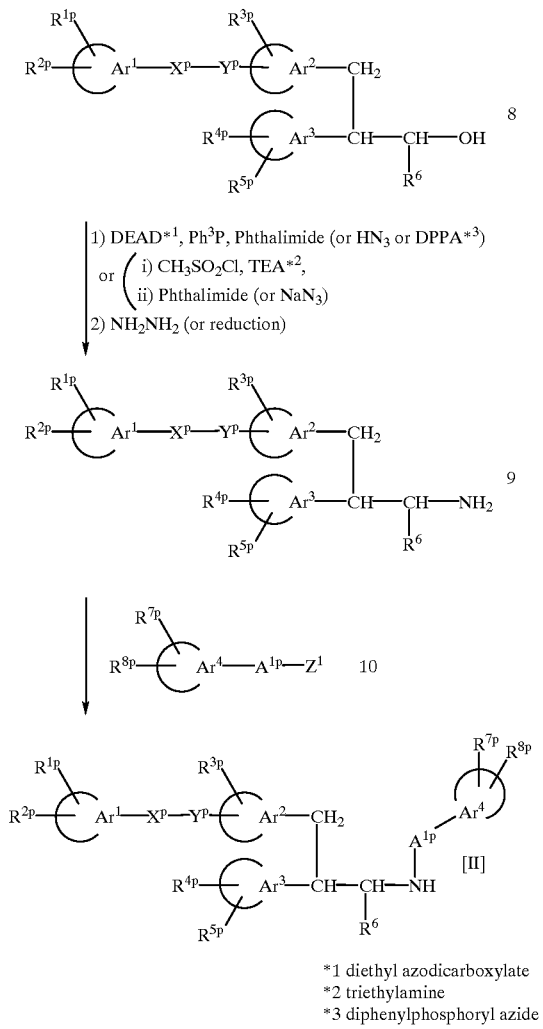

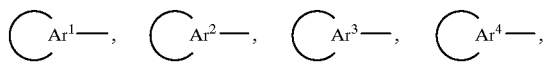

[wherein $\bigcirc Ar^1—$, $\bigcirc Ar^2—$, $\bigcirc Ar^3—$, $\bigcirc Ar^4—$, $A^{1p}$, $X^p$, $Y^p$, $Z^1$, $R^{1p}$, $R^{2p}$, $R^{3p}$, $R^{4p}$, $R^{5p}$, $R^6$, $R^{7p}$ and $R^{8p}$ are the same as defined above]

According to this process, the desired compound (II) can be prepared by firstly reacting diethyl azodicarboxylate, triphenylphosphine and phthalimide (or hydrogen azide or diphenylphosphoryl azide) or reacting a sulfonylation agent such as methanesulfonyl chloride in the presence of a base such as triethylamine, then reacting phthalimide (or sodium azide) in the presence of a base, to the alcohol compound represented by general formula 8, to obtain a phthalimide-protected form (or an azide compound) of the amine compound 9, then reacting hydrazine (or a reducing agent) to remove the phthalimido group (or reduce the azido group) to obtain an amine product represented by general formula 9, and finally reacting a compound represented by general formula 10 to the compound 9.

The above reaction steps will be described in detail referring to suitable reaction conditions, etc.

For the step of producing the compound represented by general formula 9 from the alcohol compound 8, various synthetic methods and reaction conditions well known in synthetic organic chemistry for converting alcohol compounds to amines, may be employed. For example, it is preferred to employ a so-called Mitsunobu reaction using diethyl azodicarboxylate, triphenylphosphine and phthalimide (or hydrogen azide or diphenylphosphoryl azide) or a method which comprises sulfonylation with a sulfonylating agent such as methanesulfonyl chloride in the presence of a base such as triethylamine, then reacting phthalimide (or sodium azide) in the presence of a base, and then treating (or reducing) the obtained phthalimide (or azide) compound with hydrazine.

The above reactions are conducted usually in a solvent inert to the reaction. The inert solvent may, for example, preferably be tetrahydrofuran, dimethoxyethane, benzene or toluene in the case of the above-mentioned Mitsunobu reaction; methylene chloride, chloroform, tetrahydrofuran, benzene, ethyl acetate or dimethylformamide in the case of the sulfonylation followed by the reaction with phthalimide (or sodium azide); an alcohol such as methanol or ethanol in the next step of the phthalimido-removing reaction with hydrazine; an ether such as ethyl ether or tetrahydrofuran in the case where a metal hydride complex is used as the reducing agent in the reduction reaction of the azide compound; hydrous tetrahydrofuran in the case where phosphine reduction is conducted with triphenylphosphine or the like; and an alcohol such as methanol or ethanol in the reduction by catalytic reduction.

With respect to the amounts of the reagents to be used, in the above Mitsunobu reaction, each of diethyl azodicarboxylate, triphenylphosphine and phthalimide (or hydrogen azide or diphenylphosphoryl azide) is used in an amount of 1 mol or an excess molar amount, preferably from 1 to 5 mols, per mol of the starting material alcohol compound 8. In the reaction with phthalimide (or sodium azide) after the sulfonylation, the sulfonylating agent such as methanesulfonyl chloride is used in an amount of 1 mol or an excess molar amount, preferably from 1 to 2 mols, per mol of the alcohol compound 8, and the base such as triethylamine used at that time is usually in an amount of 1 mol or an excess molar amount, preferably from 1 to 2 mols, per mol of the sulfonylating agent. In the next step of the reaction with phthalimide (or sodium azide) in the presence of a base, 1 mol or an excess molar amount, preferably from 1 to 5 mols of each of phthalimide and the base (or sodium azide) is used per mol of the sulfonylating agent. Here, the base to be used together with phthalimide is preferably sodium carbonate or potassium carbonate. Otherwise, without using such a base, a sodium salt or a potassium salt of phthalimide may be used by itself. Then, in the reaction for removing the phthalimido group with hydrazine, hydrazine is used in an amount of 1 mol or an excess molar amount, preferably from 1 to 10 mols, per mol of the phthalimide compound as the starting material compound. In the reduction of the azide compound with a metal hydride complex or with triphenylphosphine, the reducing agent is used usually in an amount of 1 mol or an excess molar amount, preferably from 1 to 2 mols, per mol of the azide compound.

In the case of the above Mitsunobu reaction, the reaction temperature is usually from −70° C. to 100° C., preferably from −20° C. to 50° C., and the reaction time is usually from 5 minutes to 48 hours, preferably from 30 minutes to 24 hours. In the reaction for removing the phthalimido group by hydrazine, the reaction temperature is usually from 0° C. to the boiling point of the solvent used for the reaction, preferably from room temperature to 100° C., and the reaction time is usually from 5 minutes to 48 hours, preferably from 30 minutes to 24 hours. In the reaction for converting the azide compound to the amine compound by reduction, when a metal hydride complex is used as the reducing agent, the reaction temperature is usually from −70° C. to 150° C., preferably from −20° C. to 50° C., and the reaction time is usually from 5 minutes to 48 hours, preferably from 10 minutes to 10 hours. When triphenylphosphine is used as the reducing agent, the reaction temperature is usually from room temperature to the boiling point of the solvent used for the reaction, preferably from 30° C. to 100° C., and the reaction time is usually from 10 minutes to 48 hours, preferably from 30 minutes to 24 hours. Further, in the case of the reduction by catalytic reduction, the reaction temperature is usually from 0° C. to 100° C., preferably from room temperature to 50° C., and the reaction time is usually from 10 minutes to 48 hours, preferably from 10 minutes to 24 hours.

The step of producing the desired compound (II) from the compound represented by general formula 9 is carried out usually in a solvent inert to the reaction and can be carried out by reacting 1 mol or an excess molar amount, preferably from 1 to 2 mols, of the alkylating agent represented by general formula 10 to 1 mol of the amine compound 9 in the presence of a base.

Such an inert solvent may, for example, be an ether such as ethyl ether, tetrahydrofuran or dioxane; an aromatic hydrocarbon such as benzene, toluene or xylene; an aprotic polar solvent such as dimethylformamide, dimethyl sulfoxide or hexamethylphosphoric triamide, or a mixture of such solvents.

The base to be used in this reaction, may, for example, be an alkali metal hydride such as sodium hydride, lithium hydride or potassium hydride; a lithium amide such as lithium amide, lithium diisopropylamide or lithium bistrimethylsilylamide; an alkyllithium such as methyllithium, butyllithium or tert-butyllithium; an alkali metal alkoxide such as sodium methoxide, sodium ethoxide or potassium tert-butoxide; an alkali metal hydroxide such as sodium hydroxide, potassium hydroxide or lithium hydroxide; or an alkali metal carbonate such as sodium carbonate or potassium carbonate.

Such a base is used usually in an amount of 1 mol or an excess molar amount, preferably from 1 to 5 mols, per mol of the starting material alkylating agent 10.

The reaction temperature is usually from −100° C. to the boiling point of the solvent used for the reaction, preferably from −80° C. to 100° C., and the reaction time is usually from 10 minutes to 48 hours, preferably from 30 minutes to 24 hours.

Further, the compound represented by general formula 10 may be commercially available or can be produced by a proper combination, as the case requires, of the methods disclosed in Reference Examples, or conventional methods or methods similar thereto.

Process D

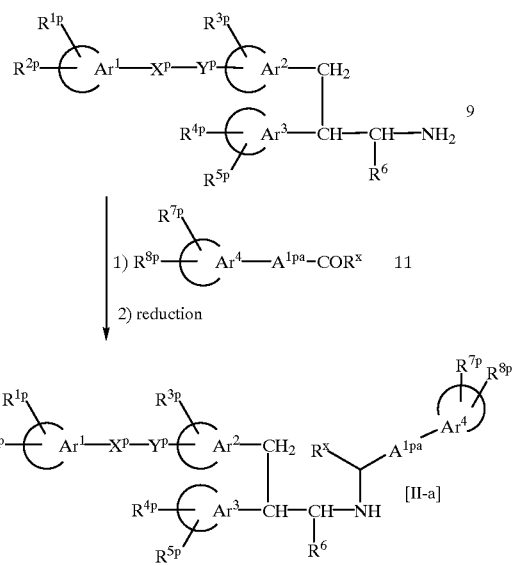

[wherein $A^{1pa}$ is a $C_{2-5}$ chain hydrocarbon group which may have substituent(s) selected from the group consisting of a halogen atom, a lower alkyl group, an oxo group, a lower hydroxyalkyl group which may be protected and a lower alkoxy group or a group represented by $—A^{1cp}—W^{1p}—A^{1bp}—$ (wherein $A^{1cp}$ is a $C_{1-4}$ chain hydrocarbon group which may have substituent(s) selected from the group consisting of a halogen atom, a lower alkyl group, an oxo group, a lower hydroxyalkyl group which may be protected and a lower alkoxy group; $A^{1bp}$ is a single bond or a $C_{1-4}$ chain hydrocarbon group which may have substituent(s) selected from the group consisting of a halogen atom, a lower alkyl group, an oxo group, a lower hydroxyalkyl group which may be protected and a lower alkoxy group; $W^{1p}$ is an oxygen atom, a sulfur atom, an ethynylene group, a cyclopropylene group or a group represented by $—NR^{wp}—$; and $R^{wp}$ is a hydrogen atom, a lower alkyl group or a protecting group for an imino group); $R^x$ is a hydrogen atom or a lower alkyl group; and

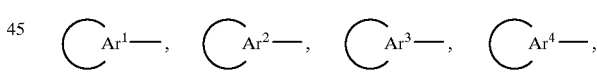

$A^{1p}, X^p, Y^p, R^{1p}, R^{2p}, R^{3p}, R^{4p}, R^{5p}, R^6, R^{7p}$ and $R^{8p}$ are the same as defined above]

According to this process, the desired compound (II-a) can usually be prepared by preliminarily forming an imine by reacting 1 mol or an excess molar amount, preferably from 1 to 2 mols of the compound represented by general formula 11 to 1 mol of the amine compound represented by general formula 9 in an inert solvent such as methanol, ethanol, benzene, ethyl ether or tetrahydrofuran, and then reducing it.

This reaction can be carried out in the same manner as the step for producing the desired compound (II) from the compound represented by general formula 6 in the above process A. Accordingly, with respect to the reaction conditions, etc., similar conditions may be employed.

Further, the compound represented by general formula 11 may be commercially available or can be produced by a proper combination, as the case requires, of the methods disclosed in Reference Examples, or conventional methods or methods similar thereto.

Process E

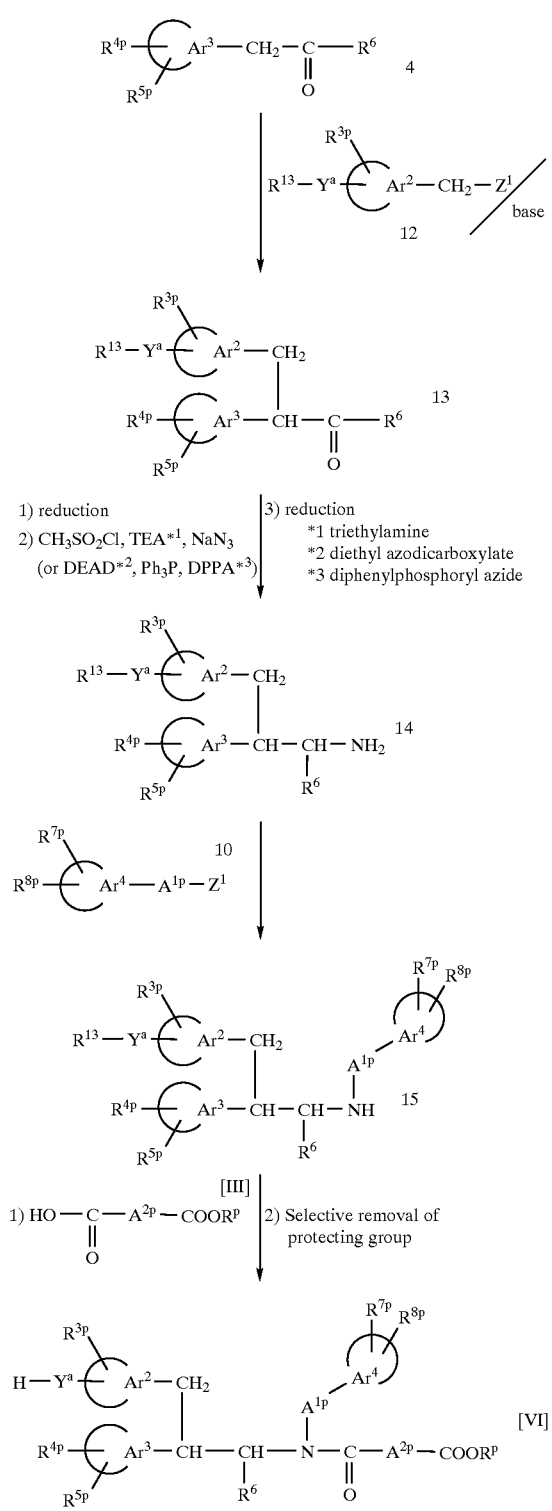

1) reduction
2) CH$_3$SO$_2$Cl, TEA*$^1$, NaN$_3$
   (or DEAD*$^2$, Ph$_3$P, DPPA*$^3$)
3) reduction
   *1 triethylamine
   *2 diethyl azodicarboxylate
   *3 diphenylphosphoryl azide 1) HO—C—A$^{2p}$—COOR$^p$
       ∥
       O
2) Selective removal of protecting group

[wherein R means a hydroxyl-protecting group when Y$^a$ is an oxygen atom; a mercapto-protecting group when Y$^a$ is a sulfur atom; or an amino- or imino-protecting group when Y$^a$ is a group represented by formula —NR$^b$— (wherein R$^b$ is the same as defined above); and

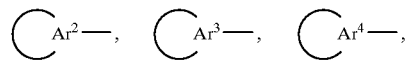

A$^{1p}$, A$^{2p}$, Y$^a$, Z$^1$, R$^{3p}$, R$^{4p}$, R$^{5p}$, R$^6$, R$^{7p}$, R$^{8p}$ and R$^p$ are the same as defined above]

According to this process, the desired compound (VI) can be prepared by firstly reacting an alkylating agent represented by general formula 12 to a ketone compound represented by general formula 4 to obtain a compound represented by general formula 13, reacting a reducing agent such as a metal hydride complex to the compound 13 to obtain an alcohol compound, then reacting diethyl azodicarboxylate, triphenylphosphine and phthalimide (or hydrogen azide or diphenylphosphoryl azide) or reacting a sulfonylating agent such as methanesulfonyl chloride in the presence of a base such as triethylamine, and then reacting phthalimide (or sodium azide) in the presence of a base, to obtain a phthalimide-protected form (or an azide compound) of the amine compound 14, then reacting hydrazine (or a reducing agent) to remove the phthalimido group (or reduce the azido group) to obtain an amine compound represented by general formula 14, reacting a compound represented by general formula 10 to the compound 14 to obtain a compound represented by general formula 15, reacting a carboxylic acid represented by general formula (III) or its reactive derivative to the compound 15, and finally selectively removing the protecting group represented by R$^{13}$.

The step of producing a compound represented by general formula 13 from a ketone compound represented by general formula 4, can be carried out in the same manner as the step of producing the compound represented by general formula 6 from the ketone represented by general formula 4 in the above process A. Accordingly, with respect to the reaction conditions, etc., similar conditions may be employed.

When R$^{13}$ is a hydroxyl-protecting group, such a hydroxyl-protecting group may be one of those disclosed above with respect to process 1.

When R$^{13}$ is a mercapto-protecting group, the hydroxyl-protecting group disclosed above with respect to process 1 can be used as such a mercapto-protecting group.

When R$^{13}$ is an amino- or imino-protecting group, such an amino- or imino-protecting group may be the amino- or imino-protecting group disclosed above with respect to process 1.

In the step of producing the amine compound represented by general formula 14 after reacting a reducing agent such as a metal hydride complex to the compound represented by general formula 13 to obtain an alcohol compound, the step of converting the compound represented by general formula 13 to the alcohol compound can be carried out in the same manner as the step of reducing the compound represented by general formula 6 to the alcohol compound 8 in the above process B. Accordingly, with respect to the reaction conditions, etc., similar conditions may be employed. Further, the step of producing an amine compound represented by general formula 14 from the obtained alcohol, can be carried out in the same manner as in the step of producing the amine compound 9 from the alcohol compound represented by general formula 8 in the above process C. Accordingly, with respect to the reaction conditions, etc., similar conditions may be employed.

The step of producing a compound represented by general formula 15 from the amine compound represented by general formula 14, can be carried out in the same manner as in the step of producing a compound represented by general formula (II) from the amine compound represented by general formula 9 in the above process C. Accordingly, with respect to the reaction conditions, etc., similar conditions may be employed.

In the step of producing the desired compound (VI) from the compound represented by general formula 15, the reaction of the compound represented by general formula 15 with the carboxylic acid represented by general formula (III) or its reactive derivative, can be carried out in the same manner as the reaction of the compound represented by general formula (II) with the carboxylic acid represented by general formula (III) or its reactive derivative in the above process 1. Accordingly, with respect to the reaction conditions, etc., similar conditions may be employed.

For the step of selectively removing the protective group represented by $R^{13}$ from the compound obtained by the above reaction, various methods may suitably be selected depending upon the type and the characteristics of the protecting group. Namely, utilizing the difference in the stability against an acid, a base or reduction between $R^{13}$ and other protecting groups, the protecting group can selectively be removed by a conventional means such as an acid, a base or reduction. With respect to specific conditions for such a reaction, the methods disclosed in known literature, such as "Protective Groups in Organic Synthesis, T. W. Greene, John Wiley & Sons (1981)", may, for example, be used.

Further, the compound represented by general formula 12 may be commercially available, or may be produced by a proper combination, as the case requires, of the methods disclosed in Reference Examples, or conventional methods or methods similar thereto.

Process F

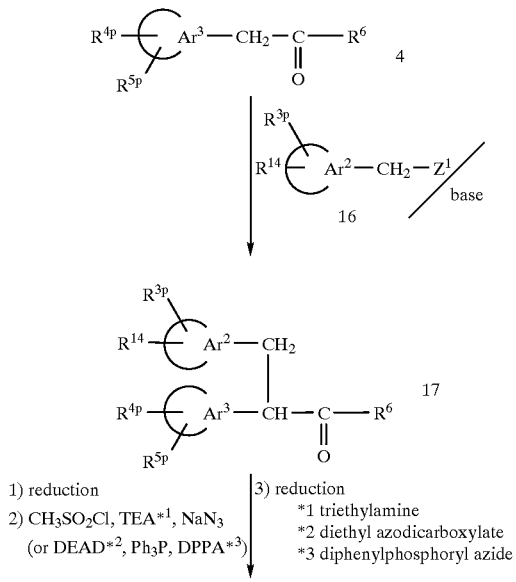

1) reduction
2) CH$_3$SO$_2$Cl, TEA*$^1$, NaN$_3$
   (or DEAD*$^2$, Ph$_3$P, DPPA*$^3$)
3) reduction
   *1 triethylamine
   *2 diethyl azodicarboxylate
   *3 diphenylphosphoryl azide

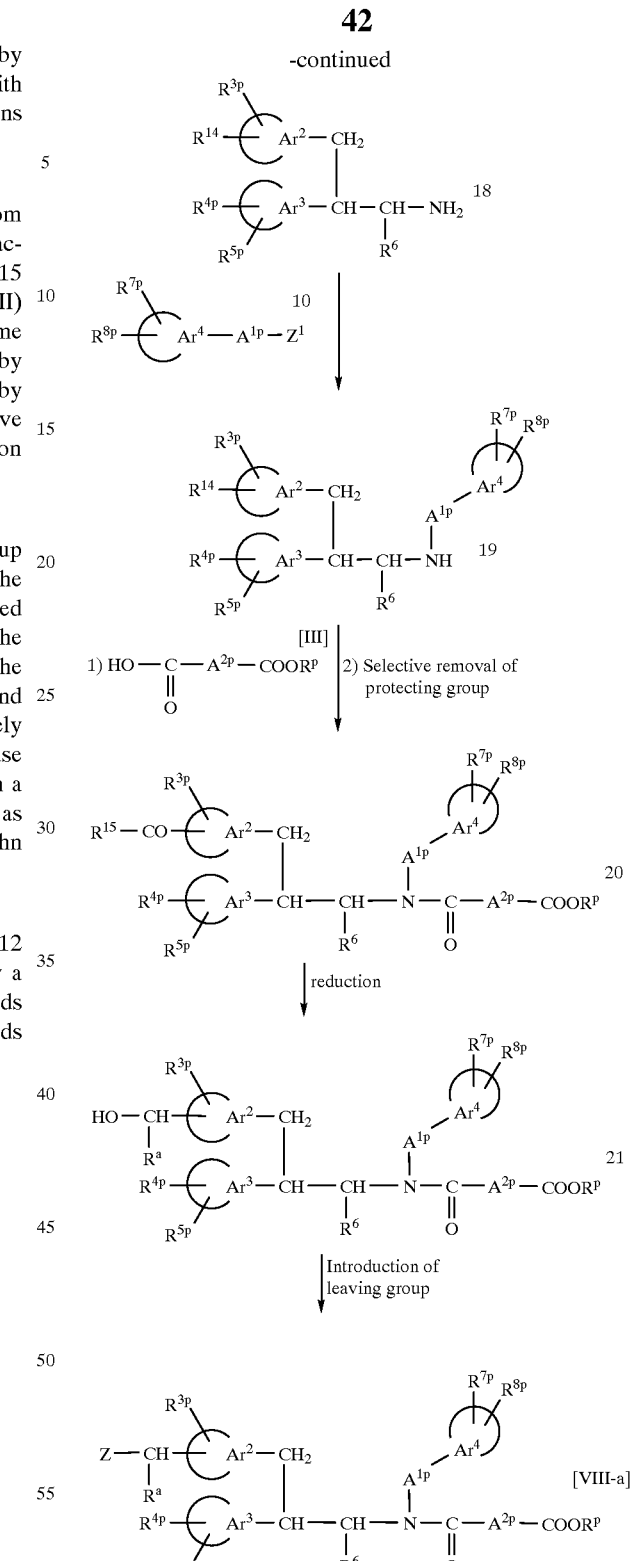

[wherein $R^{14}$ is a protected carboxyl group or a group represented by formula $R^a$—C(OR$^{p1}$)(OR$^{p2}$)— (wherein each of $R^{p1}$ and $R^{p2}$ which are the same or different, is a methyl group or an ethyl group, or $R^{p1}$ and $R^{p2}$ together represent an ethylene group, and $R^a$ is the same as defined above); $R^{15}$ is a hydroxyl group or a group represented by $R^a$ (wherein $R^a$ is the same as defined above); and

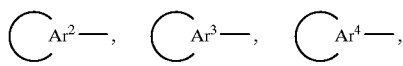

$A^{1p}$, $A^{2p}$, Z, $Z^1$, $R^{3p}$, $R^{4p}$, $R^{5p}$, $R^6$, $R_{7p}$, $R^{8p}$, $R^a$ and $R^b$ are the same as defined above]

According to this process, the desired compound (VIII-a) can be prepared by firstly reacting an alkylating agent represented by general formula 16 to a ketone compound represented by general formula 4 to obtain a compound represented by general formula 17, reacting a reducing agent such as a metal hydride complex to the compound 17 to obtain an alcohol compound, then reacting diethyl azodicarboxylate, triphenylphosphine and phthalimide (or hydrogen azide or diphenylphosphoryl azide), or reacting a sulfonylating agent such as methanesulfonyl chloride in the presence of a base such as triethylamine and then reacting phthalimide (or sodium azide) in the presence of a base, to obtain a phthalimide-protected form (or an azide compound) of the amine compound 18, then reacting hydrazine (or a reducing agent) to remove the phthalimido group (or reduce the azido group) to obtain an amine compound represented by general formula 18, reacting a compound represented by general formula 10 to the compound 18 to obtain a compound represented by general formula 19, reacting a carboxylic acid represented by general formula (III) or its reactive derivative to the compound 19, then selectively removing the protecting group at $R^{14}$ to obtain a compound represented by general formula 20, reacting a reducing agent to the compound 20 to obtain a compound represented by general formula 21, and finally introducing a leaving group to the compound 21.

The respective steps up to the production of the compound represented by general formula 20 from the ketone compound represented by general formula 4 can be carried out in the same manner as the respective steps for the production of the compound represented by general formula (VI) from the ketone compound represented by general formula 4 in the above process E. Accordingly, with respect to the reaction conditions, etc., the same conditions as in the corresponding respective steps can be employed.

The step of reacting a reducing agent to the compound represented by general formula 20 to obtain the compound represented by general formula 21, can b e conducted in the same manner as the reduction method employing e.g. sodium borohydride as a reducing agent in the step of reducing the compound represented by general formula 6 to an alcohol compound 8 in the above process B. Accordingly, with respect to the reaction conditions, etc., similar conditions can be employed.

The step of producing the desired compound (VIII-a) by introducing a leaving group to the compound represented by general formula 21 can be carried out in the same manner as in the method of introducing a leaving group to the compound represented by general formula 8 in the above process B by using, for example, a halogenating agent such as thionyl chloride, phosphorus trichloride, phosphorus pentachloride, phosphorus oxychloride, phosphorus tribromide, oxalyl chloride or phosgene, or a sulfonating agent such as methanesulfonyl chloride, p-toluenesulfonyl chloride or benzenesulfonyl chloride. Accordingly, with respect to the reaction conditions, etc., similar conditions may be employed.

Further, the compound represented by general formula 16 may be commercially available, or can be produced by a proper combination, as the case requires, of the methods disclosed in Reference Examples, or conventional methods or methods similar thereto.

Process G

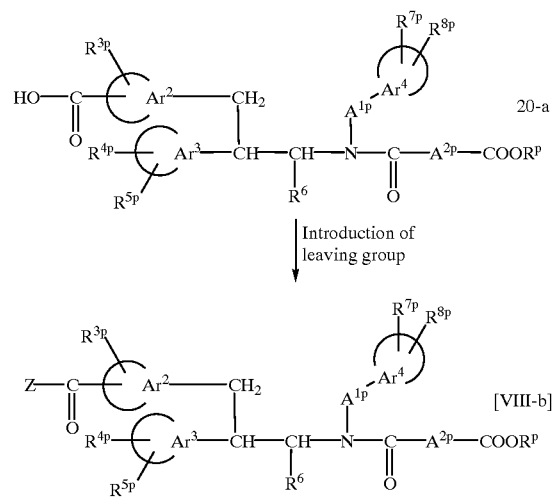

[wherein

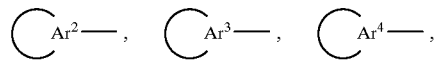

$A^{1p}$, $A^{2p}$, Z, $R^{3p}$, $R^{4p}$, $R^{5p}$, $R^6$, $R^{7p}$, $R^{8p}$ and $R^p$ are the same as defined above]

According to this process, the desired compound (VIII-b) can be prepared by introducing a leaving group to the compound represented by general formula 20-a in the same manner and conditions as the method of introducing a leaving group to the compound represented by general formula 21 in the above process F.

Process H

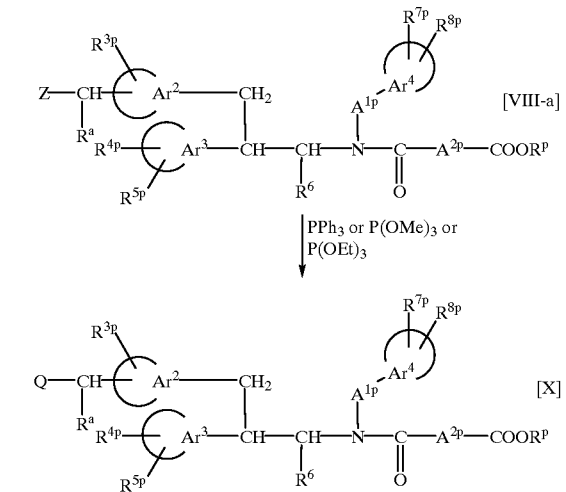

[wherein

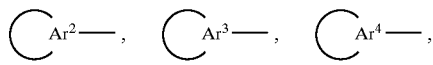

$A^{1p}$, $A^{2p}$, Q, Z, $R^{3p}$, $R^{4p}$, $R^{5p}$, $R^6$, $R^{7p}$, $R^{8p}$, $R^a$ and $R^p$ are the same as defined above]

According to this process, the desired compound (X) can be prepared by reacting triphenylphosphine, trimethyl phosphite or triethyl phosphite, to the compound represented by general formula (VIII-a).

When triphenylphosphine is reacted, the above reaction is carried out usually in an inert solvent which does not affect the reaction. As such an inert solvent, toluene or xylene is, for example, preferred.

Triphenylphosphine is used usually in an amount of 1 mol or an excess molar amount, preferably from 1 to 5 mols, per mol of the compound represented by general formula (VIII-a).

The reaction temperature is usually from room temperature to the boiling point of the solvent used for the reaction, preferably from 80° C. to 150° C. The reaction time is usually from 5 minutes to 7 days, preferably from 1 hour to 24 hours.

Likewise, when trimethyl phosphite or triethyl phosphite is reacted to the compound represented by general formula (VIII-a), the above reaction is conducted usually in an inert solvent which does not affect the reaction, or more preferably, an excess of trimethyl phosphite or triethyl phosphite is used as both the solvent and the reactant.

The reaction temperature is usually from room temperature to the boiling point of the solvent used for the reaction, preferably from 80° C. to 150° C., and the reaction time is usually from 5 minutes to 7 days, preferably from 1 hour to 24 hours.

A compound represented by general formula (XII):

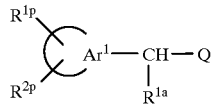

[XII]

[wherein

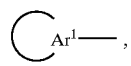

Q, $R^{1p}$, $R^{2p}$ and $R^{1a}$ are the same as defined above] can be prepared from a compound represented by general formula (XIV):

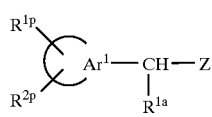

[XIV]

[wherein

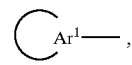

Z, $R^{1p}$, $R^{2p}$ and $R^{1a}$ are the same as defined above] in accordance with process H.

Further, the compound represented by general formula (XIV) may be commercially available, or can be prepared by a proper combination, as the case requires, of the methods disclosed in Reference Examples, or conventional methods or methods similar thereto.

Further, general formula (XIII):

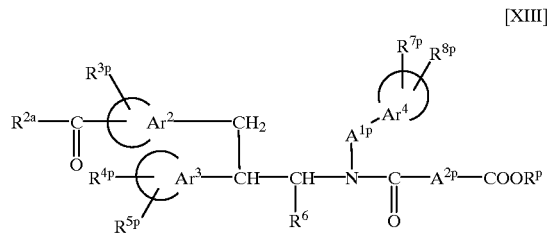

[XIII]

[wherein

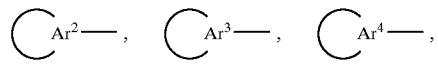

$A^{1p}$, $A^{2p}$, $R^{3p}$, $R^{4p}$, $R^{5p}$, $R^6$, $R^{7p}$, $R^{8p}$, $R^p$ and $R^{2a}$ are the same as defined above] is substantially the same as general formula 20 in the above process F, wherein $R^{15}$ is a group represented by $R^a$. Accordingly, the compound represented by general formula (XIII) can be prepared by the above process F.

Process I

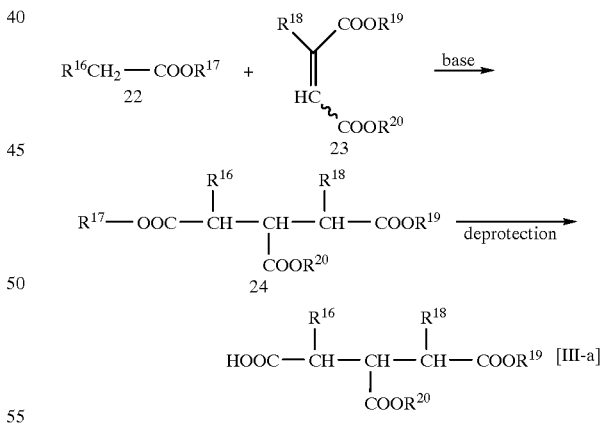

[wherein each of R and R which are the same or different, is a hydrogen atom, a lower alkyl group, an aryl group or an aralkyl group; each of $R^{19}$ and $R^{20}$ which are the same or different, is a carboxyl-protecting group; and $R^{17}$ is a tert-butyl group, a benzyl group, a benzhydryl group or a trityl group]

Process I is a process for preparing a carboxylic acid derivative represented by general formula (III-a) among the compounds represented by general formula (III).

According to this process, the desired carboxylic acid derivative (III-a) can be prepared by conducting a so-called Michael addition reaction which comprises reacting a maleic acid derivative or a fumaric acid derivative represented by general formula 23 to an ester derivative having a readily removable carboxyl-protecting group $R^{17}$, represented by general formula 22, in the presence of a base, and then removing the carboxyl-protecting group $R^{17}$ from the obtained Michael addition product 24 under a mild condition.

As the carboxyl-protecting group as $R^{19}$ and $R^{20}$, a lower alkyl group such as a tert-butyl group, or a benzhydryl group, is preferred.

The protecting group $R^{17}$ is preferably a protecting group which can readily be removed under a mild condition of catalytic reduction or weakly acidic condition and which is stable under the Michael addition reaction condition, such as a tert-butyl group, a benzyl group, a benzhydryl group or a trityl group.

The above Michael addition reaction can be conducted by reacting the compound represented by general formula 23 in an amount of 1 mol or an excess molar amount, preferably from 1 to 2 mols, to 1 mol of the compound represented by general formula 22 in the presence of a base such as sodium hydride, butyllithium, lithium diisopropylamide or lithium bis(trimethylsilyl)amide usually in an inert solvent such as benzene, ethyl ether or tetrahydrofuran.

Such a base is used usually in an amount of 1 mol or a slightly excess molar amount, preferably from 1 to 1.5 mols, per mol of the compound represented by general formula 23.

The reaction temperature is usually from −100° C. to 100° C., preferably from −80° C. to room temperature, and the reaction time is usually from 5 minutes to 24 hours, preferably from 10 minutes to 10 hours.

The reaction conditions for the reaction for removing the protecting group from the compound represented by general formula 24 to form the desired carboxylic acid derivative (III-a), vary depending upon the type of the protecting group, etc. For example, when the protecting group is a tert-butyl group, a benzhydryl group or a trityl group, a method may be employed wherein the compound is treated with an acid such as acetic acid, formic acid, trifluoroacetic acid or hydrochloric acid, preferably within a temperature range of from −20° C. to 50° C. for from 10 minutes to 24 hours in the absence of a solvent or usually in an inert solvent such as methylene chloride, anisole, tetrahydrofuran, methanol or ethanol or a solvent mixture thereof with water.

For example, when the protecting group is a benzyl group, a benzhydryl group or a trityl group, a method may be employed wherein the compound is catalytically reduced with a catalyst such as a palladium-carbon catalyst or a Raney nickel catalyst preferably under a hydrogen pressure of from 1 to 20 kg/cm² preferably within a temperature range of from 0° C. to 40° C. for from 10 minutes to 24 hours usually in an inert solvent such as methanol, ethanol, dioxane, water or acetic acid, or a solvent mixture thereof.

Among compounds represented by general formula (III-a), an optically active compound represented by general formula (III-b¹):

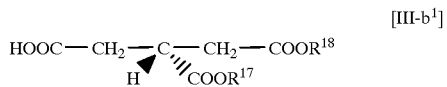

[III-b¹]

or general formula (III-b²):

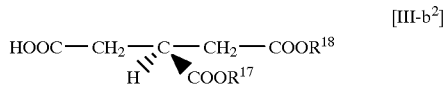

[III-b²]

[wherein each of $R^{17}$ and $R^{18}$ which are the same or different, is a carboxyl-protecting group] can be obtained by reacting a racemic mixture of the compound represented by general formula (III-b):

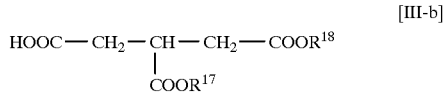

[III-b]

[wherein $R^{17}$ and $R^{18}$ are the same as defined above] with cinchonidine or quinine to obtain a mixture of two diastereomers, then separating and collecting either one of the diastereomers by utilizing the difference in the solubility between the two diastereomers, followed by recovering the free carboxylic acid by treating with an acid.

Separation of the diastereomer mixture may be conducted in an organic solvent such as carbon tetrachloride or isopropyl ether. Usually, the mixture of the diastereomers is dissolved in a solvent in a hot state, and the solution is gradually cooled to utilize the solubility difference for separation of the diastereomers.

Further, either one of the diastereomers thus obtained is treated with an acid such as hydrochloric acid to obtain an optically active compound represented by general formula (III-b¹) or (III-b²).

The compounds represented by general formula 22 and 23 may be commercially available or can be produced by a proper combination, as the case requires, of the methods disclosed in Reference Examples, or conventional methods or methods similar thereto.

Process J

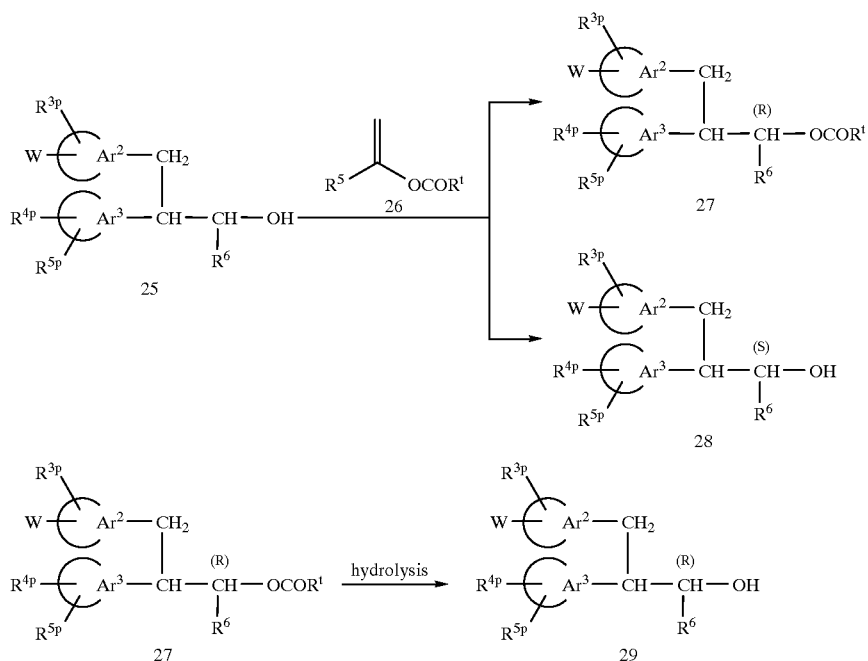

wherein W is

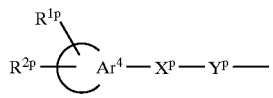

[wherein

$X^p$, $Y^p$, $R^{1p}$ and $R^{2p}$ are the same as defined above) or a group represented by $R^{13}$—$Y^a$— (wherein $Y^a$ and $R^{13}$ are the same as defined above) or $R^{14}$ (wherein $R^{14}$ is the same as defined above); $R^8$ is a hydrogen atom or a methyl group; $R^t$ is a lower alkyl group, an aryl group or an aralkyl group; and

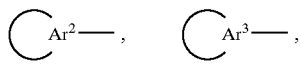

$R^{3p}$, $R^{4p}$, $R^{5p}$ and $R^6$ are the same as defined above]

Process J is a process for preparing an optically active substance 28 or 29 of the alcohol compound 25 obtainable as the above compound represented by general formula 8 or a reduction product of general formula 13 or 17.

According to this process, the desired optically active alcohol compounds 28 and 29 can be prepared by reacting a vinyl ester derivative represented by general formula 26 to a racemic alcohol derivative represented by general formula 25 in the presence of a lipase, separating the obtained optically active ester derivative 27 and the optically active alcohol derivative, and then hydrolyzing the ester group with respect to the optically active ester derivative 27.

$R^t$ of the vinyl ester derivative represented by general formula 26 is preferably a lower alkyl group such as a methyl group or an ethyl group; an aryl group such as a phenyl group or a naphthyl group; or an aralkyl group such as a benzyl group or a 2-phenylethyl group. Particularly preferred is a methyl group, i.e. a case wherein the compound represented by general formula 26 is vinyl acetate or isopropenyl acetate.

The above optical resolution reaction by lipase can be conducted usually in an inert solvent such as methylene chloride, chloroform, ethyl ether, tetrahydrofuran, benzene, toluene, hexane, heptane or acetonitrile, or by using the starting material vinyl ester derivative represented by general formula 26 itself as the solvent.

The vinyl ester derivative 26 is used usually in an amount of 1 mol or in a large excess molar amount, preferably from 1 to 100 mols, per mol of the starting material compound 25, and the amount of the lipase as the catalyst is from 0.01 to 100%, preferably from 0.1 to 20%, by weight, relative to the compound 25.

The type of the lipase is preferably a lipase TM derived from Pseudomonas sp. such as Toyothium LIP™ (manufactured by Toyobo).

Further, the above enzymatic reaction tends to be accelerated, when the reaction is carried out in the presence of a base. As a base to be used for this purpose, an organic base such as triethylamine or diisopropylethylamine, is preferred.

The base is used usually in an amount of 0.01 mol or a slightly excess molar amount, preferably from 0.1 to 1.5 mols, relative to the starting material compound 25.

The reaction temperature is usually from 0° C. to 50° C., preferably from room temperature to 40° C. The reaction time is usually from 30 minutes to 7 days, preferably from 1 hour to 48 hours.

The hydrolytic reaction of the ester represented by general formula 27 can be conducted by a common method well known in the synthetic organic chemistry under an acidic or basic condition.

Pharmacological Test 1 (Inhibitory activities against protein-farnesyl transferase)

To demonstrate the usefulness of the present invention, 50% inhibitory concentrations ($IC_{50}$ values) of the compounds of the present invention against the protein-farnesyl transferase (PFT) activities, were obtained.

(1) Preparation of PFT

PFT was separated in such a manner that a soluble fraction of rat s brain was fractionated by means of 30%–50% saturated ammonium sulfate, further dialyzed and then subjected to column chromatography by Q-sepharose™ (manufactured by Pharmacia) (Reiss et al., Cell, vol. 62, pp. 81–88 (1990)).

(2) Method for measuring PFT activities

Measurement of PFT activities was conducted by using, as a prenyl acceptor, H-ras protein or a peptide corresponding to the C-terminal 7 amino acid residues of K-rasB protein which had biotin added to the N-terminal (biotin-added Lys-Thr-Ser-Cys-Val-Ile-Met) and, as a prenyl donor, [$^3$H]-labeled farnesyl pyrophosphate (FPP) (Reiss et al., Methods: A Companion to Methods in Enzymology, vol. 1, No. 3, pp. 241–245 (1990)).

The [$^3$H]-labeled farnesyl pyrophosphate (22.5 Ci/mmol) was purchased from New England Nuclear Co. Non-labeled farnesyl pyrophosphate was chemically synthesized from ditriethylammonium phosphate, trans-trans-farnesol and trichloroacetonitrile and purified by a XAD-2-resin column and diethylaminoethylcellulose (Cornforth et al., Methods in Enzymology, vol. 15, pp. 385–390 (1969)).

H-ras protein was expressed in Escherichia coli and purified (Gibbs et al., Proc. Natl. Acad. Sci., vol. 81, pp. 5704–5708 (1984)).

The PFT reaction solution containing H-ras protein as the prenyl acceptor was 25 μl, and its composition was 50 mM Hepes pH7.5/50 μM $ZnCl_2$/5 mM $MgCl_2$/20 mM KCl/5mM DTT/0.6 μM all trans [$^3$H]-farnesyl pyrophosphate/25 μM H-ras protein/PFT derived from rat brain (Q-sepharose fraction). The reaction temperature was 37° C., the preincubation time was 10 minutes, and the reaction time was 20 minutes.

The PFT reaction solution containing biotin-added Lys-Thr-Ser-Cys-Val-Ile-Met as the prenyl acceptor, was 25 μl and its composition was 50 mM tris-Cl pH7.5/50 μM $ZnCl_2$/5 mM $MgCl_2$/20 mM KCl/1 mM DTT/0.2% n-octyl-βD-glucopyranoside/0.6 μM all trans [$^3$H]-farnesyl pyrophosphate/3.6 μM biotin-added Lys-Thr-Ser-Cys-Val-Ile-Met/PFT derived from rat brain (Q-sepharose fraction). The reaction temperature was 37° C., the preincubation time was 10 minutes, and the reaction time was 20 minutes.

The enzymatic reaction product containing H-ras protein as the prenyl acceptor, was analyzed by SDS-PAGE (sodium dodecyl sulfate/polyacrylamide gel electrophoresis). The [$^3$H]-labeled enzymatic reaction product was boiled for 3 minutes in a buffer solution containing 2% SDS/50 mM Tris-Cl pH6.8/10% sucrose/5% 2-mercaptoethanol, then subjected to 12% polyacrylamide slab gel electrophoresis whereby the [$^3$H]-labeled H-ras protein was fluorography-enhanced by EN$^3$HANCE™ (manufactured by New England Nuclear Co.) and then visualized by autoradiography (James et al., Science, vol. 260, No. 25, pp. 1937–1942 (1993)).

The measurement of PFT activities using H-ras protein as the prenyl receptor, was also analyzed by a rapid separate method. The mixed solution for measurement wherein no prenyl donor was present, was preincubated, and a prenyl group transferring reaction was initiated by an addition of [$^3$H]-FPP and terminated at an appropriate time by an addition of 0.5 ml of 4% SDS. Further, 0.5 ml of 30% trichloroacetic acid was added thereto and thoroughly mixed. Then, the reaction solution was left to stand at 4° C. for 60 minutes to let H-ras protein precipitate. This reaction solution was filtered under reduced pressure through a Whatman GF/B filter. The filter was washed 6 times with 2 ml of 6% trichloroacetic acid, and mixed with 8 ml of scintillation cocktail (Clearsol I™, manufactured by Nacalai Tesque Co.). Then, counting was carried out by a Beckmann TRI-CARB2500TR scintillation counter.

Measurement of PFT activities was also carried out by using biotin-added Lys-Thr-Ser-Cys-Val-Ile-Met as the prenyl acceptor. The mixed solution for measurement containing biotin-added Lys-Thr-Ser-Cys-Val-Ile-Met as the prenyl acceptor and containing no prenyl donor, was preincubated, and then a prenyl group transferring reaction was initiated by an addition of [$^3$H]-FPP and terminated at an appropriate time by an addition of 0.2 ml of 2 mg/ml bovine serum albumin/2% sodium dodecyl sulfate/150 mM NaCl. Further, 0.02 ml of avidin agarose (Pierce) was added thereto, and the mixture was shaked for 30 minutes to let the [$^3$H]-farnesyl group-transferred biotin-added Lys-Thr-Ser-Cys-Val-Ile-Met sufficiently bond to the avidin agarose. Then, the avidin agarose was washed four times with 1 ml of 2 mg/ml bovin serum albumin (BSA)/4% sodium dodecyl sulfate/150 mM NaCl, and mixed with 1 ml of scintillation cocktail (Clearsol I™, manufactured by Nacalai Tesque). Then, counting was carried out by a Beckmann TRI-CARB2500TR scintillation counter.

The biotin-added Lys-Thr-Ser-Cys-Val-Ile-Met heptapeptide used as an artificial substrate, was synthesized in a solid phase by an Applied biosystems model 431A peptide synthesizer, and an α-amino terminal of the solid phase Lys-Thr-Ser-Cys-Val-Ile-Met heptapeptide which was bound to a resin, was biotin-modified by N-hydroxysuccinimide biotin, then cut off from the resin and purified by reversed phase high performance liquid chromatography (HPLC).

The addition of the compound of the present invention to the PFT reaction system was carried out by preliminarily adding dimethyl sulfoxide in an amount of 1% by volume (0.25 μl) of the reaction solution.

The 50% inhibitory concentrations ($IC_{50}$ values) of the compounds of the present invention against PFT activities, are shown in Table 1.

TABLE 1

| 50% inhibitory concentrations against PFT activities | |
|---|---|
| Compound | $IC_{50}$ (nM) |
| Example 1 | 0.74 |
| Example 17 | 1.7 |

PHARMACOLOGICAL TEST EXAMPLE 2 (Inhibitory activities against farnesyl-modification of Ras protein)

Using the compounds of the present invention, inhibitory activities against farnesyl-modification of Ras protein in NIH3T3 cells transformed by activated ras gene, were measured.

The NIH3T3 cells transformed by activated ras gene, were seeded on a culture plate and cultured for 3 days. Then, a compound of the present invention in a predetermined concentration was added to the culture. In accordance with the method disclosed in J. Biol. Chem., vol. 268, p. 18415 (1993), the cells were cultured for 24 hours and then taken off from the plate, and the cells were dissolved. After centrifugal separation for 5 minutes under 12000 g, the supernatant was used as a cell extract. The cell extract was subjected to SDS polyacrylamide gel electrophoresis to separate farnesyl-modified Ras protein and non-farnesyl-modified Ras protein. The protein on the gel was transferred onto a nitrocellulose membrane, and an anti-Ras protein antibody was reacted as a probe (primary antibody reaction). An anti-primary antibody, a peroxidase inclusion (secondary antibody), was reacted, and then Ras protein was detected by a chemical fluorescence enhancing kit. The proportion of non-farnesyl-modified Ras protein was quantified by a densitometer and taken as the inhibitory activity.

The 50% inhibitory concentrations ($IC_{50}$ values) of the compounds of the present invention against farnesyl-modification of Ras protein are shown in Table 2.

TABLE 2

| 50% inhibitory concentrations against farnesyl-modification of Ras protein | |
|---|---|
| Compound | $IC_{50}$ (nM) |
| Example 1 | 1.3 |
| Example 17 | 4.3 |

From the foregoing results, the compounds of the present invention have excellent inhibitory activities against protein-farnesyl transferase (PFT) and thus useful as antitumor agents, for example, against colon cancer, pancreatic cancer, myloid leukemia, lung cancer, carcinoma cutaneum or thyroid gland cancer, particularly against pancreatic cancer.

Further, the protein-farnesyl transferase (PFT) inhibitor of the present invention is capable of inhibiting transfection of ras and capable of inhibiting reactivation of HIV gene transformed into the host cells, and thus is useful also as an anti-HIV agent.

The compound represented by general formula (I) of the present invention can be orally or parenterally administered, and it may be formulated into a formulation suitable for such administration, so that it can be used as an antitumor agent or an anti-HIV agent. To use the compound of the present invention for clinical purpose, it may be formulated into various formulations by an addition of pharmaceutically acceptable additives to meet the type of administration and then administered. As such additives, various additives which are commonly used in the field of drug formulations, may be used, including, for example, gelatin, lactose, saccharose, titanium oxide, starch, crystalline cellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropylcyclodextrin, etc.

A drug formulation to be prepared as a mixture with such additives, may, for example, be a solid formulation such as a tablet, a capsule, a granule, a powder or a suppository; or a liquid formulation such as a syrup, an elixir or an injection drug. These formulations can be prepared in accordance with conventional methods commonly employed in the field of drug formulations. Further, in the case of a liquid formulation, it may be of the type which is to be dissolved or suspended in water or in other suitable medium at the time of its use. Particularly, in the case of an injection drug, it may be dissolved or suspended in a physiological saline or in a glucose solution, and a buffering agent or a preserving agent may further be added.

These formulations may contain the compound of the present invention in a proportion of from 1.0 to 100 wt %, preferably from 1.0 to 60 wt % of the total amount. These formulations may further contain other therapeutically effective compounds.

When the compound of the present invention is used as an antitumor agent or an anti-HIV agent, its dose and the frequency of administration vary depending upon the sex, the age, the body weight and the diseased degree of the patient and the type and the range of the intended treating effects. However, in the case of an oral administration, it is preferred to administer from 0.01 to 20 mg/kg per day for an adult all at once or in a few times in a divided fashion. In the case of parenteral administration, it is preferred to administer from 0.002 to 10 mg/kg per day for an adult all at once or in a few times in a divided fashion.

The other therapeutically effective compounds may, for example, be drugs which bring about a decrease of farnesyl pyrophosphate in vivo.

The drugs which bring about a decrease of farnesyl pyrophosphate in vivo, are not particularly limited so long as they are drugs having such activities and which are acceptable as pharmaceuticals. However, biosynthesis-inhibitors against farnesyl pyrophosphate, for example, preferred. Among them, drugs which inhibit the biosynthesis of farnesyl pyrophosphate, such as hydroxymethylglutaryl CoA synthase-inhibitors or hydroxymethylglutaryl CoA reductate-inhibitors represented by e.g. lovastatin, simvastatin, pravastatin and fluvastatin disclosed, for example, in Nature, vol. 343, pp. 425–430 (1990), are preferred. Particularly preferred are hydroxymethylglutaryl CoA reductase-inhibitors such as lovastatin, simvastatin, pravastatin and fluvastatin.

The composition comprising the compound of the present invention and the above drug, can be formulated in the same manner as in the case where the compound of the present invention is used as a single drug. Such a formulation may contain the protein-farnesyl transferase inhibitor and a drug which brings about a decrease of farnesyl pyrophosphate in vivo, as active ingredients, in an amount of from 1.0 to 100 wt%, preferably from 1.0 to 60 wt %, of the entire drug.

Further, the weight ratio of the protein-farnesyl transferase inhibitor and the drug which brings about a decrease of farnesyl pyrophosphate in vivo, may be from 0.001:1 to 1000:1. However, the weight ratio is particularly preferably from 0.01:1 to 100:1.

BEST MODE FOR CARRYING OUT THE INVENTION

Now, the present invention will be described in further detail with reference to Examples and Reference Examples, but the present invention is by no means restricted by such Examples.

EXAMPLE 1

Preparation of 3-(tert-butoxycarbonyl)-4-hydroxy-4-[N-[(1R,2R)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoic acid (1) Preparation of tert-butyl (2RS,3RS)-2-[N-[(1R,2R)-1-methyl-2-(3,4-methylenedioxyphenyl)-3-{5-

(phenylcarbamoyl)-2-furyl}propyl]-N-{(E)-3-phenyl-2-propenyl}carbamoyl]-5-oxotetrahydrofuran-3-carboxylate 271 mg of N-{(E)-3-phenyl-2-propenyl}-[(1R,2R)-1-methyl-2-(3,4-methylenedioxyphenyl)-3-{5-(phenylcarbamoyl)-2-furyl}propyl]amine prepared in the same manner as in Reference Example 7, 139 mg of (2RS,3RS)-(3-tert-butoxycarbonyl)-5-oxotetrahydrofuran-2-carboxylic acid prepared in Reference Example 8 and 1.37 ml of triethylamine were dissolved in 8 ml of chloroform, and 152 mg of 2-chloro-1,3-dimethylimidazolinium chloride in 2 ml of chloroform was added under cooing with ice. The resulting reaction solution was stirred at the same temperature for 1 hour, then poured into water and extracted with ethyl acetate. The extract was dried over anhydrous magnesium sulfate. The desiccant was filtered off, and the solvent was distilled off under reduced pressure. The residue was purified by silica gel column chromatography [hexane/ethyl acetate=2/1] to give 393 mg (stoichiometric yield) of the title compound as a colorless oily substance.

(2) Preparation of methyl (3RS,4RS)-3-(tert-butoxycarbonyl)-4-hydroxy-4-[N-[(1R,2R)-1-methyl-2-(3,4-methylenedioxyphenyl)-3-{5-(phenylcarbamoyl)-2-furyl}propyl]-N-{(E)-3-phenyl-2 -propenyl}carbamoyl] butanoate 387 mg of tert-butyl (2RS,3RS)-2-[N-(1R,2R)-1-methyl-2-(3,4-methylenedioxyphenyl)-3-{5-(phenylcarbamoyl)-2-furyl}propyl]-N-{(E)-3-phenyl-2-propenyl}carbamoyl]-5-oxotetrahydrofuran-3-carboxylate was dissolved in a mixture of 10 ml of tetrahydrofuran and 5 ml of water and stirred together with 1.1 ml of 1N aqueous sodium hydroxide at room temperature for 1 hour. The reaction solution was acidified with 1N hydrochloric acid and then extracted with ethyl acetate. The extract was dried over anhydrous magnesium sulfate. The desiccant was filtered off, and the solvent was distilled off under reduced pressure. The resulting carboxylic acid was dissolved in 10 ml of ethyl acetate and mixed with a slight excess of diazomethane in ethyl ether at room temperature, and then, the solvent was distilled off under reduced pressure. The residue was purified by silica gel column chromatography [hexane/ethyl acetate=3/2] to give 387 mg (yield: 95%) of the title compound as a colorless oily substance.

(3) Preparation of methyl 3-(tert-butoxycarbonyl)-4-hydroxy-4-[N-[(1R,2R)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoate 384 mg of methyl (3RS,4RS)-3-(tert-butoxycarbonyl)-4-hydroxy-4-[N-[(1R,2R)-1-methyl-2-(3,4-methylenedioxyphenyl)-3-{5-(phenylcarbamoyl)-2-furyl}propyl]-N-{(E)-3-phenyl-2-propenyl}carbamoyl] butanoate was dissolved in 15 ml of acetonitrile and stirred together with 219 mg of tetrapropylammonium perruthenate at room temperature for 1 hour. The solvent was distilled off under reduced pressure, and the residue was preliminarily purified by silica gel short column chromatography [chloroform→methanol] and the purified again by silica gel column chromatography [hexane/ethyl acetate=2/1→3/2] to give 285 mg (yield: 74%) of the title compound as a colorless oily substance.

(4) Preparation of 3-(tert-butoxycarbonyl)-4-hydroxy-4-[N-[(1R,2R)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoic acid 285 mg of methyl 3-(tert-butoxycarbonyl)-4-hydroxy-4-[N-[(1R,2R)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoate was dissolved in a mixture of 15 ml of tetrahydrofuran and 10 ml of water and stirred together with 4 ml of 1N aqueous sodium hydroxide at room temperature for 2.5 days. The reaction solution was acidified with 1N hydrochloric acid and then extracted with ethyl acetate. The organic layer was dried over anhydrous magnesium sulfate, the desiccant was filtered off, and the solvent was distilled off under reduced pressure. The residue was purified by silica gel column chromatography [chloroform/methanol=100/1→10/1] to give 213 mg (yield: 76%) of the title compound as a colorless foamy substance.

$^1$H-NMR(CDCl$_3$) ε:1.06–1.18(3H, m), 1.40, 1.43, 1.49 and 1.50(total 9H, each s), 2.87–3.29 and 3.91–4.65(total 9H, each m), 5.79–5.91(3H, m), 6.26–7.40(14H, m), 7.52–8.28(3H, m).

FAB-MS:723(M+H)

The compounds of Examples 2 to 15 were prepared by reactions similar to those in Example 1 using the corresponding amine derivatives instead of N-{(E)-3-phenyl-2-propenyl}-[(1R,2R)-1-methyl-2-(3,4-methylenedioxyphenyl)-3-{5-(phenylcarbamoyl)-2-furyl}propyl]amine used as the starting material in Example 1.

EXAMPLE 2

3-(tert-Butoxycarbonyl)-4-hydroxy-4-[N-[(1S,2S)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoic acid $^1$H-NMR(CDCl$_3$) δ:1.06–1.18(3H, m), 1.40, 1.43, 1.49 and 1.50(total 9H, each s), 2.87–3.29 and 3.91–4. 65(total 9H, each m), 5.79–5.91(3H, m), 6.26–7.40(14H, m), 7.52–8.28(3H, m).

FAB-MS:723(M+H)

EXAMPLE 3

3-(tert-Butoxycarbonyl)-4-hydroxy-4-[N-[(1R,2R)-1-methyl-2-(4-nitrophenyl)-3-{5-(phenylcarbamoyl)-2-furyl}propyl]-N-{(E)-3-phenyl-2-propenyl}carbamoyl]-3-butenoic acid $^1$H-NMR(CDCl$_3$) δ:1.00–1.15(3H, m), 1.30–1.50(9H, m), 2.83–3.40 and 3.90–4.20(total 9H, each m), 5.65–5.80 (1H, m), 6.25–6.70(2H, m), 6.85–7.80(13H, m), 8.05–8.50 (3H, m).

FAB-MS:724(M+H)

EXAMPLE 4

3-(tert-Butoxycarbonyl)-4-[N-{(E)-3-(4-chlorophenyl)-2-propenyl}-N-[(1S,2S)-1-methyl-2-(3,4-methylenedioxyphenyl)-3-{5-(phenylcarbamoyl)-2-furyl}propyl]carbamoyl]-4-hydroxy-3-butenoic acid $^1$H-NMR(CDCl$_3$) δ:1.00–1.15(3H, m), 1.30–1.55(9H, m), 2.80–3.30(6H, m), 3.80–4.15(3H, m), 5.75–5.95(3H, m), 6.20–7.35(13H, m), 7.55–8.30(3H, m).

FAB-MS:757(M+H)

EXAMPLE 5

3-(tert-Butoxycarbonyl)-4-hydroxy-4-[N-{(E)-3-(3-methoxyphenyl)-2-propenyl}-N-[(1RS,2RS)-1-methyl-2-(3,4-methylenedioxyphenyl)-3-{5-(phenylcarbamoyl)-2-furyl}propyl]carbamoyl]-3-butenoic acid $^1$H-NMR(CDCl$_3$) δ:1.00–1.18(3H, m), 1.35–1.51(9H, m), 2.86–4.66(9H, m), 3.71–3.81(3H, m), 5.79–5.92(3H, m), 6.23–7.43(13H, m), 7.54–8.53(3H, m).

FAB-MS:753(M+H)

EXAMPLE 6

3-(tert-Butoxycarbonyl)-4-[N-{(E)-3-(2,6-dichlorophenyl)-2-propenyl}-N-[(1RS,2RS)-1-methyl-2-(3,4-methylenedioxyphenyl)-3-{5-(phenylcarbamoyl)-2 -furyl}propyl]carbamoyl]-4-hydroxy-3-butenoic acid $^1$H-NMR(CDCl$_3$)δ:1.00–1.20(3H, m), 1.30–1.50(9H, m), 2.85–3.30(6H, m), 3.80–4.70(3H, m), 5.75–5.95(3H, m), 6.30–6.80, 6.90–7.50 and 7.55–8.30(total 15H, each m).

FAB-MS:791(M+H)

EXAMPLE 7

3-(tert-Butoxycarbonyl)-4-hydroxy-4-[N-[(1R,2R)-1-methyl-2-(3,4-methylenedioxyphenyl)-3-{5-(phenylcarbamoyl)-2-furyl}propyl]-N-(3-phenylpropyl)carbamoyl]-3-butenoic acid $^1$H-NMR(CDCl$_3$) δ:0.90–1.15(3H, m), 1.30–1.50(9H, m), 1.85–2.25(2H, m), 2.50–3.50 and 4.00–4.65(total 11H, each m), 5.75–6.00(3H, m), 6.45–6.80, 6.90–7.40 and 7.55–7.90(total 15H, each m).

FAB-MS:725(M+H)

EXAMPLE 8

3-(tert-Butoxycarbonyl)-4-hydroxy-4-[N-[(1R,2R)-1-methyl-2-(3,4-methylenedioxyphenyl)-3-{5-(phenylcarbamoyl)-2-furyl}propyl]-N-(2-phenoxyethyl)carbamoyl]-3-butenoic acid $^1$H-NMR(CDCl$_3$) δ:1.05–1.20(3H, m), 1.30–1.60(9H, m), 2.85–4.00(8H, m), 4.05–4.65(3H, m), 5.70–5.95(3H, m), 6.55–7.00, 7.05–7.30 and 7.50–7.77(total 14H, each m).

FAB-MS:727(M+H)

EXAMPLE 9

3-(tert-Butoxycarbonyl)-4-hydroxy-4-[N-[(1RS, 2RS)-1-methyl-2-(3,4-methylenedioxyphenyl)-3-{5 -(phenylcarbamoyl)-2-furyl}propyl]-N-{(E)-3-(3-thienyl)-2-propenyl}carbamoyl]-3-butenoic acid $^1$H-NMR(CDCl$_3$) δ:1.08–1.13(3H, m), 1.38–1.55(9H, m), 2.88–3.30(5H, m), 3.88–4.40 and 4.55–4.65(total 4H, each m), 5.79–5.95(3H, m), 6.10–6.32(1H, m), 6.52–6.80 (4H, m), 6. 92–7.00 (1H, m), 7.10–7.40 and 7.57–7.77(total 8H, each m).

FAB-MS:729(M+H)

EXAMPLE 10

3-(tert-Butoxycarbonyl)-4-[N-{(Z)-2-chloro-3-phenyl-2-propenyl}-N-[(1RS,2RS)-1-methyl-2-(3,4-methylenedioxyphenyl)-3-{5-(phenylcarbamoyl)-2-furyl}propyl]carbamoyl]-4-hydroxy-3-butenoic acid $^1$H-NMR(CDCl$_3$) δ:1.10–1.23(3H, m), 1.35–1.50(9H, m), 2.80–3.60 and 3.90–4.60(total 9H, each m), 5.85–5.95 (3H, m), 6.50–8.20(16H, m).

FAB-MS: 757 (M+H)

EXAMPLE 11

3-(tert-Butoxycarbonyl)-4-hydroxy-4-[N-[(1R,2R)-1-methyl-2-(3,4-methylenedioxyphenyl)-3-{5-(phenylcarbamoyl)-2-furyl}propyl]-N-(3-phenyl-2-propynyl)carbamoyl]-3-butenoic acid $^1$-NMR(CDCl$_3$) δ:1.10–1.20(3H, m), 1.35–1.55(9H, m), 2.88–3.50 and 4.10–4.70(total 9H, each m), 5.85–6.00(3H, m), 6.50–7.70(14H, m), 8.15–8.30(1H, m).

FAB-MS:721(M+H)

EXAMPLE 12

3-(tert-Butoxycarbonyl)-4-hydroxy-4-[N-[(1S,2S)-1-methyl- 2-(3,4-methylenedioxyphenyl)-3-{5-(phenylcarbamoyl)-2-furyl}propyl]-N-(3-phenyl-2-propynyl)carbamoyl]-3-butenoic acid $^1$H-NMR(CDCl$_3$) δ:1.10–1.20(3H, m), 1.35–1.55(9H, m), 2.88–3.50 and 4.10–4.70(total 9H, each m), 5.85–6.00 (3H, m), 6.50–7.70(14H, m), 8.15–8.30(1H, m).

FAB-MS:721 (M+H)

EXAMPLE 13

3-(tert-Butoxycarbonyl)-4-hydroxy-4-[N-[(1RS,2RS)-1-methyl-2-(3,4-methylenedioxyphenyl)-3-{5-(phenylcarbamoyl)-2-furyl}propyl]-N-(phenylcarbamoylmethyl)carbamoyl]-3-butenoic acid $^1$H-NMR(CDCl$_3$) δ:1.05–1.20(3H, m), 1.30–1.50(9H, m), 2.70–4.80(9H, m), 5.83–5.91(3H, m), 6.54–7.80(14H, m), 8.35–9.20(2H, m).

FAB-MS:740(M+H)

EXAMPLE 14

3-(tert-Butoxycarbonyl)-4-hydroxy-4-[N-[(1RS,2RS)-1-methyl-2-(3,4-methylenedioxyphenyl)-3-{4-(phenylcarbamoyl)-2-pyridyl}propyl]-N-{(E)-3-phenyl-2-propenyl}carbamoyl]-3-butenoic acid hydrochloride $^1$H-NMR(CDCl$_3$) δ:1.01–1.18(3H, m), 1.40, 1.41, 1.48 and 1.52(total 9H, each s), 2.80–4.69(9H, ), 5.82–5.89(2H, m), 5.99–6.79(5H, m), 7.00–7.49(10H, m), 7.59–7.78(2H, m), 8.43–8.84(2H, m).

FAB-MS:734(M+H)

EXAMPLE 15

3-(tert-Butoxycarbonyl)-4-hydroxy-4-[N-[(1RS, 2RS)-1-methyl-2-(3,4-methylenedioxyphenyl)-3-{5-(phenylcarbamoyl)-2-furyl}propyl]-N-(trans-2-phenyl-1-cyclopropylmethyl)carbamoyl]-3-butenoic acid $^1$H-NMR(CDCl$_3$) δ:0.95–1.21(5H, m), 1.36–1.69(10H, m), 1.89–2.07(1H, m), 2.85–3.79 and 4.10–4.62(total 9H, each m), 5.62–5.98(3H, m), 6.40–6.79(3H, m), 6.89–8.10 (12H, m).

FAB-MS:737(M+H)

EXAMPLE 16

Preparation of 3-(ethoxycarbonyl)-4-hydroxy-4-[N-[(1RS,2RS)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoic acid 37 mg of 3-(tert-butoxycarbonyl)-4-hydroxy-4-[N-[(1RS,2RS)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoic acid prepared by reactions similar to those in Example 1 using N-{(E)-3-phenyl-2-propenyl}-[(1RS,2RS)-1-methyl-2-(3,4-methylenedioxyphenyl)-3-{5-(phenylcarbamoyl)-2-furyl}propyl]amine instead of N-{(E)-3-phenyl-2-propenyl}-[(1R,2R)-1-methyl-2-(3,4-methylenedioxyphenyl)-3-{5-(phenylcarbamoyl)-2- furyl}propyl]amine used as the starting material in Example 1 was dissolved in 10 ml of ethanol and refluxed together with 3.9 mg of hydroxylamine hydrochloride and 9.6 mg of pyridine under heating for 15 hours. The reaction solution was cooled to room temperature and evaporated to dryness under reduced pressure. The residue was purified by silica gel thin layer chromatography [Kieselgel™60F$_{254}$, Art™5744; chloroform/methanol=10/1] to give 12 mg (yield: 34%) of the title compound as a colorless foamy substance.

$^1$H-NMR(CDCl$_3$) δ:1.09–1.50(6H, m), 2.85–4.30(11H, m), 5.70–5.95(3H, m), 6.20–7.80(16H, m).

FAB-MS:695(M+H)

EXAMPLE 17

Preparation of 3-(ethoxycarbonyl)-4-hydroxy-4-[N [(1RS,2RS)-1-methyl-2-(3,4-methylenedioxyphenyl)-3-{5-(phenylcarbamoyl)-2-furyl}propyl]-N-(3-phenyl-2-propynyl)carbamoyl]-3-butenoic acid A reaction similar to that in Example 16 was carried out by using 3-(tert-butoxycarbonyl)-4-hydroxy-4-[N-[(1RS, 2RS)-1-methyl-2-(3,4-methylenedioxyphenyl)-3-{5-(phenylcarbamoyl)-2-furyl}propyl]-N-(3-phenyl-2-propynyl)carbamoyl]-3-butenoic acid as the starting material to give the title compound.

$^1$H-NMR(CDCl$_3$) δ:1.14–1.41(6H, m), 3.03–4.76(11H, m), 5.79–5.91(3H, m), 6.59–7.70(14H, m).

FAB-MS:693(M+H)

EXAMPLE 18

Preparation of 3-(isopropoxycarbonyl)-4-hydroxy-4-[N-[(1RS,2RS)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoic acid (1) Preparation of isopropyl (2RS,3RS)-2-[N-[(1RS,2RS)-1-methyl-2-(3,4-methylenedioxyphenyl)-3-{5-(phenylcarbamoyl)-2-furyl}propyl]-N-{(E)-3-phenyl-2-propenyl}carbamoyl]-5-oxotetrahydrofuran-3-carboxylate 302 mg of tert-butyl (2RS,3RS)-2-[N-{(E)-3-phenyl-2-propenyl}-[(1RS,2RS)-1-methyl-2-(3,4-methylenedioxyphenyl)-3-{5-(phenylcarbamoyl)-2-furyl}propyl]carbamoyl]-5-oxotetrahydrofuran-3-carboxylate prepared in the same manner as in Example 1(1) by using N-{(E)-3-phenyl-2-propenyl}-[(1RS,2RS)-1-methyl-2-(3,4-methylenedioxyphenyl)-3-{5-(phenylcarbamoyl)-2-furyl}propyl]amine instead of N-{(E)-3-phenyl-2-propenyl}-[(1R,2R)-1-methyl-2-(3,4-methylenedioxyphenyl)-3-{5-(phenylcarbamoyl)-2-furyl}propyl]amine used as the starting material in Example 1 was dissolved in 3 ml of formic acid and stirred at room temperature for 20 hours. The formic acid was distilled off under reduced pressure, and the residue was purified by silica gel column chromatography [chloroform/methanol= 50/1→10/1] to give 269 mg of a carboxylic acid.

65 mg of the carboxylic acid, 12 mg of isopropyl alcohol and 1.2 mg of 4-dimethylaminopyridine were dissolved in 2 ml of chloroform and stirred together with 29 mg of 1-ethyl-3-(3-dimethylaminopropyl)carbodiimide hydrochloride at room temperature for 16 hours. The reaction solution was poured into water and extracted with chloroform, and the organic layer was dried over anhydrous magnesium sulfate. The desiccant was filtered off, and the solvent was distilled off under reduced pressure. The residue was purified by silica gel column chromatography [hexane/ethyl acetate=2/ 1] to give 56 mg (yield: 81%) of the title compound as a colorless foamy substance.

(2) Preparation of 3-(isopropoxycarbonyl)-4-hydroxy-4-[N-[(1RS,2RS)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoic acid 56 mg of isopropyl (2RS,3RS)-2-[N-(1RS,2RS)-1-methyl-2-(3,4-methylenedioxyphenyl)-3-{5-(phenylcarbamoyl)-2-furyl}propyl]-N-{(E)-3-phenyl-2-propenyl}carbamoyl]-5-oxotetrahydrofuran-3-carboxylate was subjected to the same reactions as in Example 1(2) to (4) to give 10 mg (yield: 17%) of the title compound.

$^1$H-NMR(CDCl$_3$) δ:1.03–1.40(9H, m), 2.85–3.35 and 3.90–4.20(total 9H, each m), 4.95–5.20(1H, m), 5.78–6.00 (3H, m), 6.20–6.50(1H, m), 6.50–7.30(15H, m).

FAB-MS: 709 (M+H)

The compound of Examples 19 to 23 were prepared in the same manner as in Example 18 by using the corresponding alcohols instead of isopropyl alcohol used in Example 18.

EXAMPLE 19

4-Hydroxy-4-[N-[(1RS,2RS)-1-methyl-2-(3, 4-methylenedioxyphenyl)-3-{5-(phenylcarbamoyl)-2-furyl}propyl]-N-{(E)-3-phenyl-2-propenylcarbamoyl]-3-(1-methyl-2-propenyloxycarbonyl)-3-butenoic acid $^1$H-NMR(CDCl$_3$) δ: 1.00–1.50(6H, m), 2.80–3.80 and 3.90–4.80(total 9H, each m), 5.05–5.98(7H, m), 6.25–7.80 (16H, m).

FAB-MS:721 (M+H)

EXAMPLE 20

3-(Cyclobutoxycarbonyl)-4-hydroxy-4-[N-[(1RS, 2RS)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoic acid $^1$H-NMR(CDCl$_3$) δ:1.06–1.17(3H, m), 1.47–2.42(6H, m), 2.86–5.20(10H, m), 5.74–5.92(3H, m), 6.22–6.78(5H, m), 6.89–7.41(8H, m), 7.52–7.77(2H, m), 8.05–8.46(1H, m).

FAB-MS:721(M+H)

EXAMPLE 21

4-Hydroxy-4-[N-[(1RS,2RS)-1-methyl-2-(3,4-methylenedioxyphenyl)-3-{5-(phenylcarbamoyl)-2-furyl}propyl]-N-{(E)-3-phenyl-2-propenyl}carbamoyl]-3-(3-tetrahydrofuranyloxycarbonyl)-3-butenoic acid $^1$H-NMR(CDCl$_3$) δ:1.00–1.20(3H, m), 1.50–3.70(7H, m), 3.70–4.00(4H, m), 4.00–4.70(4H, m), 5.20–5.40(1H, m), 5.80–6.00(3H, m), 6.20–7.80(16H, m).

FAB-MS:737(M+H)

EXAMPLE 22

4-Hydroxy-3-(1,2-dimethylpropoxycarbonyl)-4-[N-[(1RS,2RS)-1-methyl-2-(3,4-methylenedioxyphenyl)-3-{5 -(phenylcarbamoyl)-2-furyl}propyl]-N-{(E)-3-phenyl-2-propenyl}carbamoyl]-3-butenoic acid $^1$H-NMR(CDCl$_3$)δ:0.79–0.98(6H, m), 1.05–1.22(6H, m), 1.70–1.92(1H, m), 2.88–3.32 and 3.86–5.00(total 10H, each n), 5.78–5.95(3H, m), 6.22–6.79(6H, m), 6.89–7.74(10H, n), 7.90–8.32(1H, m).

FAB-MS:737 (M+H)

EXAMPLE 23

3-(sec-Butoxycarbonyl)-4-hydroxy-4-[N-[(1RS, 2RS)-1-methyl-2-(3,4-methylenedioxyphenyl)-3-{5-(phenylcarbamoyl)-2-furyl}propyl]-N-{(E)-3-phenyl-2-propenyl}carbamoyl]-3-butenoic acid $^1$H-NMR(CDCl$_3$) δ:0.75–0.98(3H, m), 1.03–1.33(6H, m), 1.40–1.70(2H, m), 2.84–3.40 and 3.90–5.10(total 10H, each m), 5.73–5.92(3H, m), 6.23–6.78(5H, m), 6.88–7.00 (1H, m), 7.05–7.42(8H, m), 7.51–7.79(2H, m), 8.08–8.49 (1H, m).

FAB-MS:722(M+H)

REFERENCE EXAMPLE 1

Preparation of 3-methoxycinnamaldehyde 680 mg of m-anisaldehyde and 1.52 g of formylmethylenetriphenylphosphorane were dissolved in 10 ml of toluene and stirred under heating at 120 ° C. for 7 hours. The reaction solution was cooled to room temperature and purified by silica gel column chromatography [hexane/ethyl acetate=9/1→4/1] to give 199 mg of the title compound as a yellow oily substance.

REFERENCE EXAMPLE 2

Preparation of 2.6-dichlorocinnamaldehyde 146 mg of dimethylformamide in 3 ml of methylene chloride was mixed with a mixture of 0.5 ml of oxalyl chloride and 2 ml of methylene chloride under cooling with ice and stirred under a nitrogen atmosphere at the same temperature for 1 hour. The reaction solution was concentrated to dryness, and the residue was mixed with 3 ml of acetonitrile and 2 ml of tetrahydrofuran and cooled with a refrigerant. The resulting mixture was stirred together with 434 mg of 2,6-dichlorocinnamic acid and 158 mg of pyridine in 3 ml of tetrahydrofuran at the same temperature for 1 hour. After cooled to −78° C., the reaction solution was mixed with a suspension of 38 mg of copper iodide in 1 ml of tetrahydrofuran and 4.0 ml of 1M lithium tri-tert-butoxyalumino hydride in tetrahydrofuran and stirred at the same temperature for 10 minutes. After addition of 1N hydrochloric acid, the reaction solution was extracted with ethyl acetate, and the organic layer was washed with saturated aqueous sodium chloride and dried over anhydrous magnesium sulfate. The desiccant was filtered off, and the solvent was distilled off under reduced pressure. The residue was purified by silica gel thin layer chromatography [Kieselgel™60F$_{254}$, Art™5717; hexane/ethyl acetate=1/1] to give 160 mg of the title compound as a yellow oily substance.

REFERENCE EXAMPLE 3

Preparation of trans-2-phenyl-1-cyclopropanecarbaldehyde 152 mg of lithium aluminium hydride suspended in 10 ml of tetrahydrofuran was mixed with 324 mg of trans-2-phenylcyclopropane-1-carboxylic acid under cooling with ice and stirred at the same temperature for 30 minutes and then at room temperature for 2 hours. Water was gradually added to the reaction solution and then 1N hydrochloric acid was gradually added. The reaction solution was extracted with ethyl acetate, and the organic layer was dried over anhydrous magnesium sulfate. The desiccant was filtered off, and the solvent was distilled off under reduced pressure. The residue was purified by silica gel column chromatography [hexane/ethyl acetate=3/1→2/1] to give 307 mg of trans-l-(hydroxymethyl)-2-phenylcyclopropane as a colorless oily substance.

104 mg of the alcohol was dissolved in 5 ml of chloroform and stirred with 445 mg of the Dess-Martin reagent (periodinane) at room temperature for 30 minutes. The reaction solution was poured into a mixture of saturated aqueous sodium hydrogencarbonate and saturated aqueous sodium thiosulfate and extracted with ethyl acetate. The organic layer was dried over anhydrous magnesium sulfate. The desiccant was filtered off, and the solvent was distilled off under reduced pressure. The residue was purified by silica gel column chromatography [hexane/ethyl acetate=10/1] to give 52 mg of the title compound as a colorless oily substance.

REFERENCE EXAMPLE 4

Preparation of N-{(E)-3-phenyl-2-propenyl}-[(1RS, 2RS)-1-methyl-2-(4-nitrophenyl)-3-{5-(phenylcarbamoyl)-2-furyl}propyl]amine (1) Preparation of ethyl 5-{2-(4-nitrophenyl)-3-oxobutyl}-2-furancarboxylate 3.00 g of 4-nitrophenylacetone in 50 ml of dimethylformamide was mixed with 0.70 g of 60% oily sodium hydride under cooling with ice under stirring and stirred at the same temperature for 10 minutes. After addition of 3.40 g of ethyl 5-(chloromethyl)-2-furancarboxylate in 5 ml of dimethylformamide, the reaction solution was stirred at room temperature for 2.5 hours. The reaction solution was acidified with acetic acid, and water and ethyl ether were added for extraction. The organic layer was washed with saturated aqueous sodium chloride and then dried over anhydrous magnesium sulfate. The desiccant was filtered off, and the solvent was distilled off under reduced pressure. The residue was purified by silica gel column chromatography [hexane/ethyl acetate=5/1→2/1] to give 5.84 g of the title compound as a yellow oily substance.

(2) Preparation of ethyl 5-{(2RS,3SR)-3-hydroxy-2-(4-nitrophenyl)butyl}-2-furancarboxylate 5.48 g of ethyl 5-{2-(4-nitrophenyl)-3-oxobutyl}-2-furancarboxylate in 50 ml of tetrahydrofuran was mixed with 16.5 ml of 1M lithium tri-sec-butylborohydride in tetrahydrofuran under cooling at −78° C. under stirring and stirred at the same temperature for 2 hours. After addition of water, the reaction solution was stirred at room temperature for 1 hour and then extracted with ethyl acetate. The organic layer was washed with saturated aqueous sodium chloride and dried over anhydrous magnesium sulfate. The desiccant was filtered off, and the solvent was distilled off under reduced pressure. The residue was purified by silica gel column chromatography [hexane/ethyl acetate=5/1→1/1] to give 3.66 g of the title compound as a pale yellow oily substance.

(3) Preparation of ethyl 5-{(2RS,3RS)-3-amino-2-(4-nitrophenyl)butyl}-2-furancarboxylate 3.66 g of ethyl 5-{(2RS,3SR)-3-hydroxy-2-(4-nitrophenyl)butyl}-2-furancarboxylate in 40 ml of tetrahydrofuran was mixed with 4.32 g of triphenylphosphine, 2.60 ml of diethyl azodicarboxylate and 4.53 g of diphenylphosphoryl azide under cooling with ice under stirring and stirred at room temperature for 18 hours. The reaction solution was evaporated to dryness under reduced pressure, and the residue was purified by silica gel column chromatography [hexane/ethyl acetate=50/1→30/1]. The resulting azide was refluxed together with 2.37 g of triphenylphosphine in 55 ml of 10% hydrous tetrahydrofuran under heating for 6 hours. The reaction solution was cooled to room temperature, and the solvent was distilled off under reduced pressure. The residue was purified by silica gel column chromatography [ethylene chloride/methanol=100/1→20/1] to give 2.89 g of the title compound as a yellow oily substance.

(4) Preparation of ethyl 5-{(2RS,3RS)-2-(4-nitrophenyl)-3-{(E)-3-phenyl-2-propenylamino}butyl-2-furancarboxylate 500 mg of ethyl 5-{(2RS,3RS)-3-amino-2-(4-nitrophenyl)butyl}-2-furancarboxylate in 10 ml of methanol was stirred together with 199 mg of trans-cinnamaldehyde under heating at 50° C. for 3 hours. The reaction solution was cooled to 0° C. and stirred together with 57 mg of sodium borohydride at the same temperature for 15 minutes. Ethyl acetate and water were added to the reaction solution for extraction, and the organic layer was washed with saturated aqueous sodium chloride and then dried over anhydrous magnesium sulfate. The desiccant was filtered off, and the solvent was distilled off under reduced pressure. The residue was purified by silica gel column chromatography [hexane/ethyl acetate=5/2→2/1] to give 550 mg of the title compound as a yellow oily substance.

(5) Preparation of N-{(E)-3-phenyl-2-propenyl}-[(1RS,2RS)-1-methyl-2-(4-nitrophenyl)-3-{5-(phenylcarbamoyl)-2-furyl}propyl]amine 530 mg of ethyl 5-{(2RS,3RS)-2-(4-nitrophenyl)-3-{(E)-3-phenyl-2-propenylamino}butyl-2-furancarboxylate was dissolved in a mixture of 5 ml of tetrahydrofuran and 5 ml of methanol and stirred together with 5 ml of 1N aqueous sodium hydroxide at room temperature for 15 hours. The reaction solution was acidified with 1N hydrochloric acid and extracted with ethyl acetate, and the extract was dried over anhydrous magnesium sulfate. The desiccant was filtered off, and the solvent was distilled off under reduced pressure. The residue was dissolved in 5 ml of dimethylformamide and stirred together with 220 mg of aniline and 339 mg of 1-ethyl-3-(3-dimethylaminopropyl)carbodiimide hydrochloride at room temperature for 17 hours. After addition of water, the reaction solution was extracted with ethyl acetate. The extract was washed with 1N aqueous sodium hydroxide and saturated aqueous sodium chloride and dried over anhydrous magnesium sulfate. The desiccant was filtered off, and the solvent was distilled off under reduced pressure. The residue was purified by silica gel column chromatography [hexane/ethyl acetate=2/1→1/1] to give 356 mg of the title compound as a pale yellow oily substance.

N-{(E)-3-Phenyl-2-propenyl}-[(1RS,2RS)-1-methyl-2-(3,4-methylenedioxyphenyl)-3-(5-(phenylcarbamoyl)-2-furyl}propyl]amine, N-(3-phenyl-2-propynyl)-[(1RS,2RS)-1-methyl-2-(3,4-methylenedioxyphenyl)-3-{5-(phenylcarbamoyl)-2-furyl}propyl]amine, N-{(E)-3-(3-methoxyphenyl)-2-propenyl}-[(1RS,2RS)-1-methyl-2-(3,4-methylenedioxyphenyl)-3-{5-(phenylcarbamoyl)-2-furyl}propyl]amine, N-{(E)-3-(2,6-dichlorophenyl)-2-propenyl}-[(1RS,2RS)-1-methyl-2-(3,4-methylenedioxyphenyl)-3-{5-(phenylcarbamoyl)-2-furyl}propyl]amine, N-{(E)-3-(3-thienyl)-2-propenyl}-[(1RS,2RS)-1-methyl-2-(3,4-methylenedioxyphenyl)-3-{5-(phenylcarbamoyl)-2-furyl}propyl]amine, N-{(Z)-2-chloro-3-phenyl-2-propenyl}-[(1RS,2RS)-1-methyl-2-(3,4-methylenedioxyphenyl)-3-{5-(phenylcarbamoyl)-2-furyl}propyl]amine, N-{(E)-3-phenyl-2-propenyl}-[(1RS,2RS)-1-methyl-2-(3,4-methylenedioxyphenyl)-3-{4-(phenylcarbamoyl)-2-pyridyl}propyl]amine and N-(trans-2-phenyl-1-cyclopropylmethyl)-[(1RS,2RS)-1-methyl-2-(3,4-methylenedioxyphenyl)-3-{4-(phenylcarbamoyl)-2-pyridyl}propyl]amine were prepared in the same manner as in Reference Example 4 by using the corresponding arylacetone derivatives and/or halides and/or aldehyde derivatives instead of 4-nitrophenylacetone and/or ethyl 5-(chloromethyl}-2-furancarboxylate and/or trans-cinnamaldehyde used as the starting materials in Reference Example 4.

REFERENCE EXAMPLE 5

Preparation of 2-(chloromethyl)-5-(phenylcarbamoyl)furan (1) Preparation of 5-(phenylcarbamoyl)-2-furfural diethyl acetal 20.0 g of 2-furfural diethyl acetal in 200 ml of ethyl ether was mixed with 75 ml of 1.68M n-butyllithium in hexane at −78° C. under a nitrogen atmosphere and stirred at the same temperature for 30 minutes and then at room temperature for 30 minutes. The reaction solution was cooled to −78° C. again, and 14.0 ml of phenyl isocyanate was added. Then, the reaction solution was stirred at room temperature for 17 hours. After addition of saturated aqueous ammonium chloride, the reaction solution was extracted with ethyl acetate, and the organic layer was washed with 1N hydrochloric acid, water, saturated aqueous sodium hydrogencarbonate and saturated aqueous sodium chloride successively and dried over anhydrous magnesium sulfate. The desiccant was filtered off, and the solvent was distilled off under reduced pressure. The residue was purified by silica gel column chromatography [hexane/ethyl acetate=10/1→1/1] to give 25.9 g of the title compound as a colorless oily substance.

(2) Preparation of 5-(phenylcarbamoyl)-2-furfural 25.2 g of 5-(phenylcarbamoyl)-2-furfural diethyl acetal in 200 ml of chloroform was mixed with 50 ml of trifluoroacetic acid under cooling with ice and stirred at the same temperature for 3 hours. The reaction solution was diluted with chloroform, washed with water, saturated aqueous sodium hydrogencarbonate and saturated aqueous sodium chloride successively and dried over anhydrous sodium sulfate. The desiccant was filtered off, and the solvent was distilled off under reduced pressure. The residue was purified by silica gel column chromatography [hexane/ethyl acetate=10/1→1/1] to give 12.5 g of the title compound as a colorless oily substance.

(3) Preparation of 2-(chloromethyl)-5-(phenylcarbamoyl)furan 12.4 g of 5-(phenylcarbamoyl)-2-furfural in 200 ml of methanol was mixed with 3.5 g of sodium borohydride under cooling with ice and stirred at the same temperature for 10 minutes and then at room temperature for 1 hour. After water was added under cooling with ice, the reaction solution was stirred at room temperature for 30 minutes, and the solvent was distilled off under reduced pressure. The residue was mixed with ethyl ether, washed with 1N hydrochloric acid, water, saturated aqueous sodium hydrogencarbonate and saturated aqueous sodium chloride successively and dried over anhydrous sodium sulfate. The desiccant was filtered off, and the solvent was distilled off under reduced pressure. The residue was purified by silica gel column chromatography [hexane/ethyl acetate=1/1→1/2] to give 10.3 g of an alcohol.

5.40 g of the alcohol was dissolved in 100 ml of chloroform and mixed with 2.0 ml of thionyl chloride under cooling at −60° C. The reaction solution was stirred at 0° C. for 1 hour, mixed with water and extracted with ethyl acetate. The organic layer was washed with water, saturated aqueous sodium hydrogencarbonate and saturated aqueous sodium chloride successively and dried over anhydrous sodium sulfate. The desiccant was filtered off, and the solvent was distilled off under reduced pressure. The residue was purified by silica gel column chromatography [hexane/ethyl acetate=3/1] to give 4.55 g of the title compound as a colorless oily substance.

REFERENCE EXAMPLE 6

Preparation of N-(phenylcarbamoylmethyl)-[(1RS,2RS)-1-methyl-2-(3,4-methylenedioxyphenyl)-3-{5-(phenylcarbamoyl)-2-furyl}propyl]amine (1) Preparation of N-(methoxycarbonylmethyl)-[(1RS,2RS)-1-methyl-2-(3,4-methylenedioxyphenyl)-3-{5-(phenylcarbamoyl)-2-furyl}propyl]amine 200 mg of N-[(1RS,2RS)-1-methyl-2-(3,4-methylenedioxyphenyl)-3-{5-(phenylcarbamoyl)-2-furyl}propyl]amine prepared in the same manners as in Reference Example 4(1) to (3) by using 3,4-methylenedioxyphenylacetone and 2-(chloromethyl)-5-phenylcarbamoylfuran prepared in Reference Example 5 instead of 4-nitrophenylacetone and ethyl 5-(chloromethyl)-2-furancarboxylate used as the starting materials in Reference Example 4 was dissolved in 3 ml of dimethylformamide, and 88 mg of potassium carbonate was added. 88 mg of methyl bromoacetate was added under cooling with ice, and the resulting solution was stirred at room temperature for 15 hours. The reaction solution was poured into water and extracted with ethyl acetate, and the organic layer was washed with water and saturated aqueous sodium chloride and then dried over anhydrous magnesium sulfate. The desiccant was filtered off, and the solvent was distilled off under reduced pressure. The residue was purified by silica gel thin layer chromatography [Kieselgel™60F$_{254}$, Art™5717; hexane/ethyl acetate=1/1] to give 159 mg of the title compound as a colorless foamy substance.

(2) Preparation of N-(phenylcarbamoylmethyl)-[(1RS,2RS)-1-methyl-2-(3,4-methylenedioxyphenyl)-3-{5-(phenylcarbamoyl)-2-furyl}propyl]amine 159 mg of N-(methoxycarbonylmethyl)-[(1RS,2RS)-1-methyl-2-(3,4-methylenedioxyphenyl)-3-{5-(phenylcarbamoyl)-2-furyl}propyl]amine in 5 ml of tetrahydrofuran was stirred together with 0.3 ml of 4N aqueous sodium hydroxide at room temperature for 1.5 hours. The reaction solution was acidified with 1N hydrochloric acid and then extracted with ethyl acetate, and the extract was dried over anhydrous magnesium sulfate. The desiccant was filtered off, and the solvent was distilled off under reduced pressure. The residue was dissolved in 3 ml of dimethylformamide and stirred together with 161 mg of aniline and 98 mg of 1-ethyl-3-(3-dimethylaminopropyl)carbodiimide hydrochloride at room temperature for 17 hours. After addition of water, the reaction solution was extracted with ethyl acetate, and the extract was washed with 1N aqueous sodium hydroxide and saturated aqueous sodium chloride and dried over anhydrous magnesium sulfate. The desiccant was filtered off, and the solvent was distilled off under reduced pressure. The residue was purified by silica gel thin layer chromatography [Kieselgel™60F$_{254}$, Art™5717; hexane/ethyl acetate=1/1] to give 102 mg of the title compound as a colorless foamy substance.

REFERENCE EXAMPLE 7

Preparation of N-{(E)-3-phenyl-2-propenyl}-[(1R,2R)-1-methyl-2-(4-nitrophenyl)-3-{5-(phenylcarbamoyl)-2-furyl}propyl]amine (1) Preparation of ethyl 5-{(2R,3S)-3-hydroxy-2-(4-nitrophenyl)butyl}-2-furancarboxylate 6.35 g of ethyl 5-{(2RS,3SR)-3-hydroxy-2-(4-nitrophenyl)butyl}-2-furancarboxylate [the compound prepared in Reference Example 4(2)] was dissolved in 64 ml of vinyl acetate, and 2.66 ml of triethylamine was added. Then, 635 mg of immobilized lipase (Toyothium LIP) was added, and the reaction solution was stirred at room temperature for 5 days. The insolubles were filtered off, and the filtrate was evaporated under reduced pressure. The residue was purified by silica gel column chromatography [hexane/ethyl acetate=7/2→2/1] to give 2.93 g of ethyl 5-{(2S,3R)-3-acetoxy-2-(4-nitrophenyl)butyl}-2-furancarboxylate and 2.81 g of the title compound as colorless oily substances, respectively. The absolute steric configuration of the title compound was determined by the Mosher method (J.Am.Chem.Soc.), vol. 113, p. 4092 (1991)).

(2) Preparation of N-{(E)-3-phenyl-2-propenyl}-[(1R,2R)-1-methyl-2-(4-nitrophenyl)-3-{5-(phenylcarbamoyl)-2-furyl}propyl]amine The title compound was prepared in the same manners as in Reference Example 4(3) to (5) by using ethyl 5-{(2R,3S)-3-hydroxy-2-(4-nitrophenyl)butyl}-2-furancarboxylate as the starting material.

N-{(E)-3-Phenyl-2-propenyl}-[(1S,2S)-1-methyl-2-(4-nitrophenyl)-3-{5-(phenylcarbamoyl)-2-furyl}propyl]amine was prepared in the same manner as in (2) from ethyl 5-{(2S,3R)-3-hydroxy-2-(4-nitrophenyl)butyl}-2-furancarboxylate obtained by alkali hydrolysis of ethyl 5-{(2S,3R)-3-acetoxy-2-(4-nitrophenyl)butyl}-2-furancarboxylate prepared in (1) as described above.

N-{(E)-3-Phenyl-2-propenyl}-[(1R,2R)-1-methyl-2-(3,4-methylenedioxyphenyl)-3-{5-(phenylcarbamoyl)-2-furyl}propyl]amine, N-((E)-3-phenyl-2-propenyl}-[(1S,2S)-1-methyl-2-(3,4-methylenedioxyphenyl)-3-{5-(phenylcarbamoyl)-2-furyl}propyl]amine, N-{(E)-3-(4-chlorophenyl)-2-propenyl}-[(1S,2S)-1-methyl-2-(3,4-methylenedioxyphenyl)-3-{5-(phenylcarbamoyl)-2-furyl}propyl]amine, N-(3-phenylpropyl)-[(1R,2R)-1-methyl-2-(3,4-methylenedioxyphenyl)-3-{5-(phenylcarbamoyl)-2-furyl}propyl]amine, N-(2-phenoxyethyl)-[(1R,2R)-1-methyl-2-(3,4-methylenedioxyphenyl)-3-{5-(phenylcarbamoyl)-2-furyl}propyl]amine, N-(3-phenyl-2-propynyl)-[(1R,2R)-1-methyl-2-(3,4-methylenedioxyphenyl)-3-{5-(phenylcarbamoyl)-2-furyl}propyl]amine and N-(3-phenyl-2-propynyl)-[(1S,2S)-1-methyl-2-(3,4-methylenedioxyphenyl)-3-{5-(phenylcarbamoyl)-2-furyl}propyl]amine were prepared in the same manner as in Reference Example 7 by using the corresponding arylacetone derivatives and/or aldehyde derivatives instead of 4-nitrophenylacetone and/or trans-cinnamaldehyde used as the starting materials in Reference Example 7.

REFERENCE EXAMPLE 8

Preparation of (2RS,3RS)-3-(tert-butoxycarbonyl)-5-oxotetrahydrofuran-2-carboxylic acid (1) Preparation of (2RS,3SR)-2-(benzyloxycarbonyl)-5-oxotetrahydrofuran-3-carboxylic acid 5.2 g of (2RS,3SR)-5-oxotetrahydrofuran-2,3-dicarboxylic acid in 88 ml of acetone was stirred together with 6.5 g of 1,1'-dicyclohexylcarbodiimide at room temperature for 2 hours. After addition of 3.26 ml of benzyl alcohol, the reaction solution was stirred at the same temperature for 12 hours. The insolubles were filtered off, and the filtrate was concentrated under reduced pressure. The residue was purified by silica gel column chromatography [hexane/ethyl acetate=4/1→chloroform/methanol=50/1] to give 7.93 g of the title compound as a yellow solid.

(2) Preparation of 2-benzyl 3-tert-butyl (2RS,3RS)-5-oxotetrahydrofuran-2,3-dicarboxylate 7.93 g of (2RS,3SR)-(2-benzyloxycarbonyl)-5-oxotetrahydrofuran-3-carboxylic acid in 75 ml of chloroform was mixed with 5.5 g of 4-dimethylaminopyridine, 8.6 g of 1-ethyl-3-(3-dimethylaminopropyl)carbodiimide hydrochloride and 5.7 ml of tert-butyl alcohol successively, and stirred at room temperature for 60 hours. The reaction solution was poured into 1N hydrochloric acid cooled with ice and extracted with ethyl acetate, and the organic layer was dried over anhydrous magnesium sulfate. The desiccant was filtered off, and the solvent was distilled off under reduced pressure. The residue was purified by silica gel column chromatography [hexane/ethyl acetate=5/1] to give 6.48 g of the title compound as a white solid.

(3) Preparation of (2RS,3RS)-3-(tert-butoxycarbonyl)-5-oxotetrahydrofuran-2-carboxylic acid 4.92 g of 2-benzyl 3-tert-butyl (2RS,3RS)-5-oxotetrahydrofuran-2,3-dicarboxylate in 50 ml of ethyl acetate was catalytically reduced with 500 mg of a 10% palladium-carbon catalyst at room temperature under atmospheric pressure of hydrogen for 3 hours. The catalyst was filtered off, and the filtrate was evaporated to dryness under reduced pressure to give 3.44 g of the title compound as a white solid.

REFERENCE EXAMPLE 9

Preparation of (2S,3S)-3-(tert-butoxycarbonyl)-5-oxotetrahydrofuran-2-carboxylic acid (1) Preparation of 3-tert-butyl 1,2-diethyl (1S,2R)-1-hydroxy-1,2,3-propanetricarboxylate 31 ml of 1.69M n-butyllithium in hexane was dissolved in 30 ml of tetrahydrofuran, and 7.1 ml of diisopropylamine was added under cooling with ice. The resulting solution was stirred at the same temperature for 30 minutes at then cooled to −78° C. 4.94 g of diethyl (S)-malate in 20 ml of tetrahydrofuran was added dropwise at −50° C. or below, and the reaction solution was stirred at −20° C. for 1.5 hours. The reaction solution was cooled to −78° C., and a solution of 5.58 g of tert-butyl bromoacetate and 4.66 g of hexamethylphosphoric triamide in 20 ml of tetrahydrofuran was added dropwise at −50° C. or below. Then, the reaction solution was stirred at room temperature for 1 hour. The reaction solution was poured into 150 ml of 0.5N hydrochloric acid and extracted with diethyl ether, and the organic layer was washed with saturated aqueous sodium hydrogencarbonate and saturated aqueous sodium chloride and dried over anhydrous magnesium sulfate. The desiccant was filtered off, and the solvent was distilled off under reduced pressure. The residue was purified by silica gel column chromatography [hexane/ethyl acetate=5/1→4/1] to give 3.8 g of the title compound as a yellow oily substance.

(2) Preparation of (2S,3R)-5-oxotetrahydrofuran-2,3-dicarboxylic acid 16.49 g of 3-tert-butyl 1,2-diethyl (1S,2R)-1-hydroxy-1,2,3-propanetricarboxylate, 100 ml of acetic acid and 50 ml of concentrated hydrochloric acid were mixed and stirred at 70° C. for 5 hours. The acetic acid and the hydrochloric acid were distilled off under reduced pressure, and the residue was dissolved in 100 ml of acetic acid and 50 ml of concentrated hydrochloric acid again. The resulting solution was stirred at 70° C. for 12 hours. The acetic acid and the hydrochloric acid were distilled off under reduced pressure, and the residue was mixed with 100 ml of trifluoroacetic acid and stirred at 60° C. for 5 hours. The trifluoroacetic acid was distilled off under reduced pressure, and the residue was crystallized from hexane/ethyl acetate to give 9.38 g of the title compound as a white powder.

(3) Preparation of (2S,3S)-3-(tert-butoxycarbonyl)-5-oxotetrahydrofuran-2-carboxylic acid The title compound was prepared in the same manner as in Reference Example 8 by using (2S,3R)-5-oxotetrahydrofuran-2,3-dicarboxylic acid as the starting material.

INDUSTRIAL APPLICABILITY

The compound of the present invention has excellent protein-farnesyl transferase (PFT) inhibitory activities and is useful as an antitumor agent or an anti-HIV agent.

We claim:

1. A compound represented by general formula (I) or a pharmaceutically acceptable salt or ester thereof:

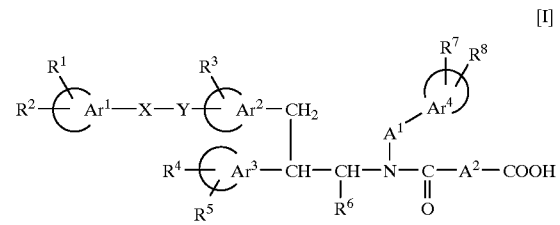

[I]

wherein each of

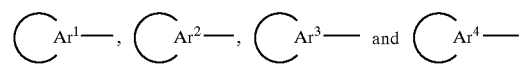

which are the same or different, is an aryl group or an aromatic heterocyclic group; $A^1$ is a $C_{2-6}$ chain hydrocarbon group which may have substituent(s) selected from the group consisting of a halogen atom, a lower alkyl group, an oxo group, a lower hydroxyalkyl group and a lower alkoxy group or a group represented by —$A^{1a}$—$W^1$—$A^{1b}$— (wherein $A^{1a}$ is a $C_{1-4}$ chain hydrocarbon group which may have substituent(s) selected from the group consisting of a halogen atom, a lower alkyl group, an oxo group, a lower hydroxyalkyl group and a lower alkoxy group; $A^{1b}$ is a single bond or a $C_{1-4}$ chain hydrocarbon group which may have substituent(s) selected from the group consisting of a halogen atom, a lower alkyl group, an oxo group, a lower hydroxyalkyl group and a lower alkoxy group; $W^1$ is an oxygen atom, a sulfur atom, an ethynylene group, a cyclopropylene group or a group represented by —$NR^W$—; and $R^W$ is a hydrogen atom or a lower alkyl group); $A^2$ is a $C_{2-8}$ chain hydrocarbon group which may have substituent(s) selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and an aralkyl group; each of X and Y which are the same or different, is an oxygen atom, a sulfur atom, a carbonyl group or a group represented by —$CHR^a$— (wherein $R^a$ is a hydrogen atom or a lower alkyl group) or by —$NR^b$— (wherein $R^b$ is a hydrogen atom or a lower alkyl group), or X and Y together represent a vinylene group or an ethynylene group; each of $R^1$, $R^2$, $R^3$, $R^7$ and $R^8$ which are the same or different, is a hydrogen atom, a halogen atom, a hydroxyl group, a lower alkyl group, a lower alkenyl group or a lower alkoxy group; each of $R^4$ and $R^5$ which are the same or different, is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; and $R^6$ is a lower alkyl group, provided that when one of X and Y is an oxygen atom, a sulfur atom or a group represented by —$NR^b$— (wherein $R^b$ is the same as defined above), the other is a carbonyl group or a group represented by —$CHR^a$— (wherein $R^a$ is the same as defined above).

2. The compound according to claim 1, wherein X is a group represented by —$NR^b$— (wherein $R^b$ is a hydrogen atom or a lower alkyl group), and Y is a carbonyl group.

3. The compound according to claim 1, wherein X is an oxygen atom, and Y is a group represented by —$CHR^a$— (wherein $R^a$ is a hydrogen atom or a lower alkyl group).

4. The compound according to claim 1, wherein each of X and Y is a group represented by —$CHR^a$— (wherein $R^a$ is a hydrogen atom or a lower alkyl group).

5. The compound according to claim 1, wherein X and Y together represent a vinylene group.

6. The compound according to claim 1, wherein $A^1$ is a group represented by —$CH_2CH=CH$—, —$CH_2C\equiv C$—, —$CH_2CH_2O$— or —$CH_2CH_2CH_2$—.

7. The compound according to claim 1, wherein $A^2$ is a group represented by formula (a):

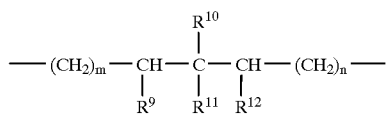

[a]

(wherein $R^9$ is a hydrogen atom, a hydroxyl group, a lower hydroxyalkyl group, a lower alkoxy group or a carboxyl group; $R^{10}$ is a hydrogen atom, a halogen atom, a hydroxyl group, a lower alkoxy group, a carboxyl group or a lower carboxyalkyl group; $R^{11}$ is a hydrogen atom, a lower hydroxyalkyl group, a carboxyl group, a lower alkoxycarbonyl group or a lower alkenyloxycarbonyl group; $R^{12}$ is a hydrogen atom, a halogen atom, a hydroxyl group or a carboxyl group; and each of m and n which are the same or different, is an integer of from 0 to 2).

8. The compound according to claim 1, wherein $A^2$ is a group represented by formula (b):

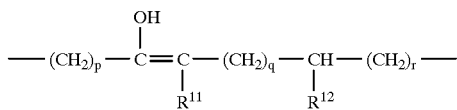

[b]

(wherein $R^{11}$ is a hydrogen atom, a lower hydroxyalkyl group, a carboxyl group, a lower alkoxycarbonyl group or a lower alkenyloxycarbonyl group; $R^{12}$ is a hydrogen atom, a hydroxyl group or a carboxyl group; p is 0 or 1; and each of q and r which are the same or different, is an integer of from 0 to 2).

9. An antitumor agent which comprises a compound represented by general formula (I) or a pharmaceutically acceptable salt or ester thereof:

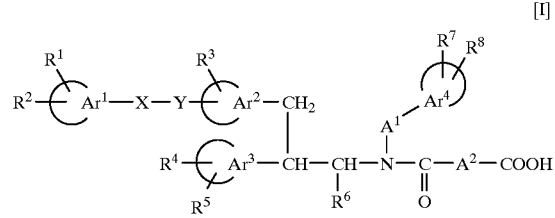

[I]

[wherein each of

which are the same or different, is an aryl group or an aromatic heterocyclic group; $A^1$ is a $C_{2-6}$ chain hydrocarbon group which may have substituent(s) selected from the group consisting of a halogen atom, a lower alkyl group, an oxo group, a lower hydroxyalkyl group and a lower alkoxy group or a group represented by —$A^{1a}$—W—$A^{1b}$— (wherein $A^{1a}$ is a $C_{1-5}$ chain hydrocarbon group which may have substituent(s) selected from the group consisting of a halogen atom, a lower alkyl group, an oxo group, a lower hydroxyalkyl group and a lower alkoxy group; $A^{1b}$ is a single bond or a $C_{1-4}$ chain hydrocarbon group which may have substituent(s) selected from the group consisting of a halogen atom, a lower alkyl group, an oxo group, a lower hydroxyalkyl group and a lower alkoxy group; $W^1$ is an oxygen atom, a sulfur atom, an ethynylene group, a cyclopropylene group or a group represented by —$NR^W$—; and $R^W$ is a hydrogen atom or a lower alkyl group); $A^2$ is a $C_{2-8}$ chain hydrocarbon group which may have substituent(s) selected from the group consisting of a halogen atom, a lower alkyl group, a hydroxyl group, a lower hydroxyalkyl group, a lower alkoxy group, a carboxyl group, a lower alkoxycarbonyl group, a lower alkenyloxycarbonyl group, a lower carboxyalkyl group, an aryl group and an aralkyl group; each of X and Y which are the same or different, is an oxygen atom, a sulfur atom, a carbonyl group or a group represented by —$CHR^a$— (wherein $R^a$ is a hydrogen atom or a lower alkyl group) or by —$NR^b$— (wherein $R^b$ is a hydrogen atom or a lower alkyl group), or X and Y together represent a vinylene group or an ethynylene group; each of $R^1$, $R^2$, $R^3$, $R^7$ and $R^8$ which are the same or different, is a hydrogen atom, a halogen atom, a hydroxyl group, a lower alkyl group, a lower alkenyl group or a lower alkoxy group; each of $R^4$ and $R^5$ which are the same or different, is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; and $R^6$ is a lower alkyl group, provided that when one of X and Y is an oxygen atom, a sulfur atom or a group represented by —$NR^b$— (wherein $R^b$ is the same as defined above), the other is a carbonyl group or a group represented by —$CHR^a$— (wherein $R^a$ is the same as defined above)], as an active ingredient.

* * * * *